US012544235B2

(12) United States Patent
Atwood

(10) Patent No.: US 12,544,235 B2
(45) Date of Patent: Feb. 10, 2026

(54) EXPANDABLE INTERVERTEBRAL SPACERS

(71) Applicant: DeGen Medical, Inc., Florence, SC (US)

(72) Inventor: Kyle Atwood, Darlington, SC (US)

(73) Assignee: DeGen Medical, Inc., Florence, SC (US)

( * ) Notice: Subject to any disclaimer, the term of this patent is extended or adjusted under 35 U.S.C. 154(b) by 519 days.

(21) Appl. No.: 17/587,367

(22) Filed: Jan. 28, 2022

(65) Prior Publication Data

US 2022/0151801 A1 May 19, 2022

Related U.S. Application Data

(63) Continuation of application No. 16/747,994, filed on Jan. 21, 2020, now Pat. No. 11,234,829.

(60) Provisional application No. 62/794,840, filed on Jan. 21, 2019.

(51) Int. Cl.
*A61F 2/44* (2006.01)
*A61F 2/30* (2006.01)

(52) U.S. Cl.
CPC .. *A61F 2/4425* (2013.01); *A61F 2002/30556* (2013.01); *A61F 2002/30891* (2013.01); *A61F 2002/443* (2013.01)

(58) Field of Classification Search
CPC ........... A61F 2/4455–2/447; A61F 2250/0004; A61F 2250/001; A61F 2250/0048
See application file for complete search history.

(56) References Cited

U.S. PATENT DOCUMENTS

| | | | |
|---|---|---|---|
| 5,653,763 | A | 8/1997 | Errico et al. |
| 5,961,554 | A | 10/1999 | Janson et al. |
| 5,980,572 | A | 11/1999 | Kim et al. |
| 6,102,950 | A | 8/2000 | Vaccaro |
| 6,129,763 | A | 10/2000 | Chauvin et al. |
| 6,176,882 | B1 | 1/2001 | Biedermann et al. |

(Continued)

FOREIGN PATENT DOCUMENTS

| | | |
|---|---|---|
| CN | 101460117 | 6/2009 |
| CN | 101049254 | 5/2010 |

(Continued)

OTHER PUBLICATIONS

Aesculap Implant Systems, LLC, "CeSpace XP Interbody System," p. 1, retrieved from Internet Apr. 24, 2014, <URL: http://www.aesculapimplantsystems.com/default.aspx?pageid=3945>.

(Continued)

*Primary Examiner* — Eduardo C Robert
*Assistant Examiner* — Holly Joanna Lane
(74) *Attorney, Agent, or Firm* — MacMillan, Sobanski & Todd, LLC

(57) ABSTRACT

The description relates to an expandable intervertebral spacer configured to engage an intervertebral disk. An example expandable spacer includes a main body, a first endplate, a second endplate, a driving member, a plurality of pins, and an actuation member. The expandable spacer is configured to transition from a first configuration to a second configuration by various structures (e.g., steps, faceted surfaces, curved surfaces, multi-faceted portions) defined on the first endplate, the second endplate, and the driving member.

16 Claims, 16 Drawing Sheets

(56) References Cited

U.S. PATENT DOCUMENTS

| | | | |
|---|---|---|---|
| 6,375,682 | B1 | 4/2002 | Fleischmann et al. |
| 6,443,989 | B1 | 9/2002 | Jackson |
| 6,491,724 | B1 | 12/2002 | Ferree |
| 6,558,424 | B2 | 5/2003 | Thalgott |
| 6,562,074 | B2 | 5/2003 | Gerbec et al. |
| 6,685,742 | B1 | 2/2004 | Jackson |
| 6,743,257 | B2 | 6/2004 | Castro |
| 6,761,739 | B2 | 7/2004 | Shepard |
| 7,018,415 | B1 | 3/2006 | McKay |
| 7,037,339 | B2 | 5/2006 | Houfburg |
| 7,094,257 | B2 | 8/2006 | Mujwid et al. |
| 7,137,997 | B2 | 11/2006 | Paul |
| 7,220,280 | B2 | 5/2007 | Kast et al. |
| 7,396,365 | B2 | 7/2008 | Michelson |
| 7,708,779 | B2 | 5/2010 | Edie et al. |
| D629,104 | S | 12/2010 | Calverley et al. |
| 7,875,078 | B2 | 1/2011 | Wysocki et al. |
| 7,875,080 | B2 | 1/2011 | Puno et al. |
| 8,025,680 | B2 | 9/2011 | Hayes et al. |
| 8,057,548 | B2 | 11/2011 | Abernathie et al. |
| 8,062,375 | B2 | 11/2011 | Glerum et al. |
| 8,114,092 | B2 | 2/2012 | Altarac et al. |
| 8,267,939 | B2 | 9/2012 | Cipoletti et al. |
| 8,303,879 | B2 | 11/2012 | Bertele et al. |
| 8,328,872 | B2 | 12/2012 | Duffield et al. |
| 8,337,530 | B2 | 12/2012 | Hestad et al. |
| 8,394,145 | B2 | 3/2013 | Weiman |
| 8,425,604 | B2 | 4/2013 | Trieu |
| D682,427 | S | 5/2013 | Farris et al. |
| 8,496,706 | B2 | 7/2013 | Ragab et al. |
| 8,496,713 | B2 | 7/2013 | Bennett et al. |
| 8,506,629 | B2 | 8/2013 | Weiland |
| 8,518,120 | B2 | 8/2013 | Glerum et al. |
| 8,523,910 | B2 | 9/2013 | Seifert et al. |
| 8,545,566 | B2 | 10/2013 | Niemiec et al. |
| 8,551,176 | B2 | 10/2013 | Ulrich, Jr. et al. |
| 8,556,974 | B2 | 10/2013 | Suh et al. |
| 8,556,979 | B2 | 10/2013 | Glerum et al. |
| 8,597,355 | B2 | 12/2013 | Hansell |
| 8,597,359 | B2 | 12/2013 | Butler et al. |
| 8,617,244 | B2 | 12/2013 | Reichen et al. |
| 8,632,593 | B2 | 1/2014 | Suh et al. |
| 8,641,768 | B2 | 2/2014 | Duffield et al. |
| 8,679,183 | B2 | 3/2014 | Glerum et al. |
| 8,685,064 | B2 | 4/2014 | Hestad et al. |
| 8,685,098 | B2 | 4/2014 | Glerum et al. |
| 8,696,751 | B2 | 4/2014 | Ashley et al. |
| 8,709,086 | B2 | 4/2014 | Glerum |
| 8,888,853 | B2 | 11/2014 | Glerum et al. |
| 8,888,854 | B2 | 11/2014 | Glerum et al. |
| 8,900,309 | B2 | 12/2014 | James et al. |
| 8,926,704 | B2 | 1/2015 | Glerum et al. |
| 9,039,771 | B2 | 5/2015 | Glerum et al. |
| 9,119,730 | B2 | 9/2015 | Glerum et al. |
| 9,155,628 | B2 | 10/2015 | Glerum et al. |
| 9,204,974 | B2 | 12/2015 | Glerum et al. |
| 9,211,196 | B2 | 12/2015 | Glerum et al. |
| 9,216,095 | B2 | 12/2015 | Glerum et al. |
| 9,216,096 | B2 | 12/2015 | Lynn et al. |
| 9,226,836 | B2 | 1/2016 | Glerum |
| 9,289,244 | B2 | 3/2016 | Hestad et al. |
| 9,358,126 | B2 | 6/2016 | Glerum et al. |
| 9,358,128 | B2 | 6/2016 | Glerum et al. |
| 9,452,063 | B2 | 9/2016 | Glerum et al. |
| 9,456,903 | B2 | 10/2016 | Glerum et al. |
| 9,492,287 | B2 | 11/2016 | Glerum et al. |
| 9,510,954 | B2 | 12/2016 | Glerum et al. |
| 9,532,810 | B2 | 1/2017 | Hestad et al. |
| 9,597,200 | B2 | 3/2017 | Glerum et al. |
| 9,655,747 | B2 | 5/2017 | Glerum et al. |
| 9,757,248 | B2 | 9/2017 | Chokshi |
| 9,763,700 | B1 | 9/2017 | Gregory |
| 9,848,997 | B2 | 12/2017 | Glerum et al. |
| 9,949,841 | B2 | 4/2018 | Glerum et al. |
| 9,962,271 | B2 | 5/2018 | Glerum |
| 10,034,767 | B2 | 7/2018 | Baynham |
| 10,052,213 | B2 | 8/2018 | Glerum et al. |
| 10,098,758 | B2 | 10/2018 | Matthew et al. |
| 10,154,912 | B2 | 12/2018 | Glerum |
| 10,219,913 | B2 | 3/2019 | Matthew et al. |
| 10,226,359 | B2 | 3/2019 | Glerum et al. |
| 10,299,934 | B2 | 5/2019 | Seifert et al. |
| 10,314,721 | B2 | 6/2019 | Chokshi |
| 10,327,917 | B2 | 6/2019 | Glerum et al. |
| 10,350,081 | B2 | 7/2019 | Seifert et al. |
| 10,350,085 | B2 | 7/2019 | Glerum et al. |
| 10,463,501 | B2 | 11/2019 | Black et al. |
| 2004/0102850 | A1 | 5/2004 | Shepard |
| 2005/0149192 | A1 | 7/2005 | Zucherman et al. |
| 2007/0032871 | A1 | 2/2007 | Michelson |
| 2007/0073400 | A1 | 3/2007 | Paul |
| 2007/0293948 | A1 | 12/2007 | Bagga et al. |
| 2009/0076616 | A1 | 3/2009 | Duggal et al. |
| 2009/0171461 | A1 | 7/2009 | Conner et al. |
| 2009/0198278 | A1 | 8/2009 | Shibata et al. |
| 2010/0286779 | A1 | 11/2010 | Thiobodeau |
| 2011/0040384 | A1 | 2/2011 | Junn et al. |
| 2011/0160860 | A1 | 6/2011 | Johnston et al. |
| 2011/0172769 | A1 | 7/2011 | Ganem et al. |
| 2011/0172774 | A1 | 7/2011 | Varela |
| 2011/0184522 | A1 | 7/2011 | Melkent et al. |
| 2011/0190888 | A1 | 8/2011 | Bertele et al. |
| 2011/0224796 | A1 | 9/2011 | Weiland et al. |
| 2011/0307016 | A1 | 12/2011 | Reglos et al. |
| 2012/0078370 | A1 | 3/2012 | James et al. |
| 2012/0089191 | A1 | 4/2012 | Altarac et al. |
| 2012/0136443 | A1 | 5/2012 | Wenzel |
| 2012/0316649 | A1 | 12/2012 | Johnston et al. |
| 2013/0030544 | A1 | 1/2013 | Studer |
| 2013/0060339 | A1 | 3/2013 | Duffield et al. |
| 2013/0131726 | A1 | 5/2013 | Suh et al. |
| 2013/0144388 | A1 | 6/2013 | Emery et al. |
| 2013/0158667 | A1 | 6/2013 | Tabor et al. |
| 2013/0158669 | A1 | 6/2013 | Sungarian et al. |
| 2014/0012382 | A1 | 1/2014 | Doty |
| 2014/0163682 | A1 | 6/2014 | Iott et al. |
| 2014/0236297 | A1 | 8/2014 | Iott et al. |
| 2014/0277474 | A1 | 9/2014 | Robinson et al. |
| 2015/0100128 | A1 | 4/2015 | Glerum et al. |
| 2015/0100129 | A1 | 4/2015 | Waugh et al. |
| 2015/0272743 | A1 | 10/2015 | Jimenez et al. |
| 2015/0342748 | A1 | 12/2015 | Baynham |
| 2015/0342749 | A1* | 12/2015 | Baynham ................ A61F 2/447 623/17.16 |
| 2015/0366675 | A1* | 12/2015 | Matthews ............... A61F 2/447 623/17.16 |
| 2016/0095716 | A1* | 4/2016 | Baynham ................ A61F 2/447 623/17.16 |
| 2017/0035577 | A1 | 2/2017 | Iott et al. |
| 2017/0156885 | A1 | 6/2017 | Zur et al. |
| 2017/0216045 | A1* | 8/2017 | Dewey .................. A61F 2/4611 |
| 2017/0281432 | A1 | 10/2017 | Glerum et al. |
| 2018/0014947 | A1* | 1/2018 | Baynham .............. A61F 2/4455 |
| 2018/0161071 | A1 | 6/2018 | Gregory |
| 2018/0193164 | A1* | 7/2018 | Shoshtaev ............. A61F 2/4425 |
| 2018/0207002 | A1 | 7/2018 | Glerum et al. |
| 2018/0289508 | A1 | 10/2018 | Glerum |
| 2018/0338840 | A1 | 11/2018 | Glerum et al. |
| 2019/0021871 | A1 | 1/2019 | Baynham |
| 2019/0083279 | A1* | 3/2019 | Suddaby ................. A61F 2/447 |
| 2019/0282374 | A1 | 9/2019 | Chokshi |

FOREIGN PATENT DOCUMENTS

| | | |
|---|---|---|
| EP | 2025307 | 2/2009 |
| EP | 2942036 | 11/2015 |
| WO | 2011047230 | 4/2011 |
| WO | 2013152257 | 10/2013 |
| WO | 2013158960 | 10/2013 |
| WO | 2014028635 | 2/2014 |
| WO | 2014071268 | 5/2014 |
| WO | 2014093430 | 6/2014 |
| WO | 2014151165 | 9/2014 |

(56) References Cited

FOREIGN PATENT DOCUMENTS

| | | |
|---|---|---|
| WO | 2014165319 | 10/2014 |
| WO | 2015198335 | 12/2015 |
| WO | 2017189416 | 11/2017 |

OTHER PUBLICATIONS

Synthes Spine, "Advanced ACF Spacer: An allograft spacer with demineralized surfaces for anterior cervical Interbody fusion.," Synthes.com, 2004, pp. 1-7.
Lemcke, et al., "Polyetheretherketone (PEEK) Spacers for Anterior Cervical Fusion: A Retrospective Comparative Effectiveness Clinical Trial," Open Orthop. J., 2011, vol. 5, pp. 348-353.
Bonovo Orthopedics, "NuVasive PCM Cervical Disc," pp. 1-9, accessed Feb. 26, 2014, http://www.ponovo-ortho.com/Products/Spine(Cervical).php.
Depuy Spine, "Surgical Technique," VG2 Cervical Allograft, Brochure from Depuy Spine, 2003, pp. 1-12.
Globus Medical, "Sustain & Sustain-R, Large, Trapezoidal thoracolumbar vertebral body replacement device," retrieved from Internet Feb. 26, 2014, <URL:http://www.globusmedical.com/portfolio/sustain-sustain-r-large/>, pp. 1-3.
Globus Medical, "Colonial, cervical interbody fusion device," retrieved from Internet Feb. 26, 2014, <URL: http://globusmedical.com/portfolio/colonial/>, pp. 1-2.
*Globus Medical Inc.* v. *Depuy Synthes Products, LLC, Depuy Synthes Sales, Inc.*, Complaint, Case No. 1:13-cv-00854-UNA, 2013, at pp. 1-5.
Ho, et al., "Kurokawa-type Laminoplasty using Hydroxyapatite Spacer for Cervical Myelopathy," Hong Kong J. Orthop Surg, 2004, vol. 8 (1), pp. 12-21.
Mahe Medical, "Implants Cervical" retrieved from www.slideshare.net, slide No. 10, accessed Feb. 26, 2014, http://image.slidesharecdn.com/cages-130721071738-phpapp02/95/slide-10-638.jpg?cb=1374409152.
Niu, et al., "Trapezoidal Titanium Cage in Anterior Cervical Interbody Fusion: A Clinical Experience," Chang Gung Med. J., 2005, vol. 28, No. 4, pp. 212-221.
Nutech Medical, "Interbody," Nutchmedical.com, accessed Feb. 26, 2014, http://nutechmedical.com/products/spine/interbody/, pp. 1-3.
Gelisim Medical, "Spinal Cerrahi", Gelisimmedikal.com accessed Jun. 27, 2014, http://www.gelisimmedikal.com/eng/servical-peek-cage.asp., 2013, pp. 1-2.
Atlas Spine, "HiJAK AC," retrieved from Internet Mar. 5, 2019, <URL: https://www.atlasspine.com/hijak-ac>.
Frisch et al. "Static versus Expandable Interbody Spacers: Preliminary 1-Year Clinical and Radiographic Results," Journal of Clinical Neurology, Neurosurgery and Spine, 2017, vol. 1, No. 1, pp. 1-9.
Exactech Spine, "Octane M Modular PEEK Spacer System," retrieved from Internet, pp. 1-16.

* cited by examiner

EXPANDABLE INTERVERTEBRAL SPACERS

RELATED APPLICATIONS

This application is a continuation of U.S. Nonprovisional application Ser. No. 16/747,994, filed on Jan. 21, 2020, now U.S. Pat. No. 11,234,829, which claims the benefit of U.S. Provisional Application No. 62/794,840, filed on Jan. 21, 2019. The entire disclosure of each of these related applications is hereby incorporated by reference into this disclosure.

FIELD

The disclosure relates to the field of implantable medical devices. More particularly, the disclosure relates to medical devices suitable for implantation in spaces between bones, such as spaces between vertebral bodies in a spinal column of a vertebrate. Specific examples relate to expandable spacers suitable for implantation between adjacent vertebral bodies in a spinal column.

BACKGROUND

Bone degeneration can be caused by trauma, disease, and natural processes, such as aging, which can have a negative impact on the lifestyle of an animal. For example, destabilization of a spine in a vertebrate, such as a human being, may result in alteration of the spacing between the adjacent vertebral bodies. This destabilization can place pressure onto the surrounding nerves and tissues between the vertebral bodies causing pain, discomfort, and, eventually, nerve damage.

One approach to alleviating the pain and discomfort caused by the destabilization of the spacing between the adjacent vertebral bodies is to implant a medical device commonly referred to as an intervertebral spacer, or simply a spacer, into the space between two adjacent vertebral bodies. The intervertebral spacer supports the structure of the spine by maintaining a desired spacing between adjacent intervertebral bodies and proper angular positioning of the spinal column.

Some intervertebral spacers are static devices that provide a spacer having fixed dimensions. Expandable intervertebral spacers are dynamic devices that allow for controlled expansion in situ. These expandable spacers provide several benefits, including reduction of the trialing required to identify and select an appropriate spacer for implantation and reduction of impaction of the adjacent vertebral bodies that can occur during insertion. Overall, expandable spacers offer a clinician an ability to optimize the fit of the spacer between intervertebral bodies during placement.

Despite the existence of various expandable spacers in the art, a need for improved expandable intervertebral spacers remains.

BRIEF SUMMARY OF SELECTED EXAMPLES

An example expandable spacer includes a main body, a first endplate, a second endplate, a driving member, a plurality of pins, and an actuation member. The main body has at least one opening. The first endplate has a first endplate first end, a first endplate second end, at least one first endplate extension disposed between the first endplate first end and the first endplate second end that has at least one opening, a first endplate top surface, a first endplate bottom surface that defines at least one first endplate protruding member that extends between the first endplate first end to the first endplate second end. The second endplate has a second endplate first end, a second endplate second end, at least one second endplate extension disposed between the first endplate first end and the first endplate second end that has at least one opening, a second endplate top surface, a second endplate bottom surface that defines at least one second endplate protruding member extending between the second endplate first end to the second endplate second end. The driving member has a driving member first end, a driving member second end, at least one driving member extension disposed between the driving member first end and the driving member second end, the at least one driving member extension includes at least one opening. The actuation member is configured to be inserted into the driving member to transition the expandable spacer from a first configuration to a second configuration. The plurality of pins has at least two pins, each pin includes a first end and a second end. The first end or the second end of each pin passes through and is received by one opening disposed on the main body, one opening disposed on the first endplate, one opening disposed on the second endplate, and one opening disposed on the driving member to assemble the main body, the first endplate, the second endplate, and the driving member together.

Another example expandable spacer includes a main body, a first endplate, a second endplate, a driving member, a plurality of pins, and an actuation member. The main body has at least two openings. The first endplate has a first endplate first end, a first endplate second end, at least one first endplate extension disposed between the first endplate first end and the first endplate second end that includes at least one opening, a first endplate top surface, a first endplate bottom surface that defines at least two first endplate protruding members that extends between the first endplate first end to the first endplate second end, at least four slots that extends between the first endplate top surface and first endplate bottom surface. The second endplate has a second endplate first end, a second endplate second end, at least one second endplate extension disposed between the first endplate first end and the first endplate second end that includes at least one opening, a second endplate top surface, a second endplate bottom surface that defines at least two second endplate protruding members that extends between the second endplate first end to the second endplate second end, at least four slots that extends between the second endplate top surface and the second endplate bottom surface. The driving member has a driving member first end, a driving member second end, at least two driving member extensions disposed between the driving member first end and the driving member second end, the at least two driving member extensions each includes at least one opening. The actuation member is configured to be inserted into the driving member to transition the expandable spacer from a first configuration to a second configuration. The plurality of pins has at least four pins, each pin includes a first end and a second end. The first end or the second end of each pin passes through and is received by one opening disposed on the main body, one opening disposed on the first endplate, one opening disposed on the second endplate, and one opening disposed on the driving member to assemble the main body, the first endplate, the second endplate, and the driving member together.

Another example expandable spacer includes a main body, a first endplate, a second endplate, a driving member, a plurality of pins, and an actuation member. The main body has a main body first set of openings and a main body second set of openings. The first endplate has a first endplate first end, a first endplate second end, a first extension disposed between the first endplate first end and the first endplate second end that includes a first set of oblong openings, a second extension disposed between the first endplate first end and the first endplate second end that includes a second set of oblong openings, a first endplate top surface, a first endplate bottom surface that defines first and second protruding members that extend between the first endplate first end to the first endplate second end, and the first endplate defines a first, second, third, fourth, and fifth slots that extend between the first endplate top surface and first endplate bottom surface. The second endplate has a second endplate first end, a second endplate second end, a third extension disposed between the second endplate first end and the second endplate second end that includes a third set of oblong openings, a fourth extensions disposed between the second endplate first end and the second endplate second end that includes a fourth set of oblong openings, a second endplate top surface, a second endplate bottom surface defines third and fourth protruding members that extends between the second endplate first end to the second endplate second end, the second endplate includes a sixth, seventh, eighth, ninth, and tenth slots that extend between the second endplate top surface and second endplate bottom surface. The driving member has a driving member first end, a driving member second end, a driving member first extension disposed toward the driving member first end that includes first and second sets of steps and a first opening, a driving member second extension disposed toward the driving member first end that includes third and fourth sets of steps and a second opening, a driving member third extension disposed toward the driving member second end that includes fifth and sixth sets of steps and a third opening, a driving member fourth extension disposed toward the driving member second end that includes seventh and eighth sets of steps and a fourth opening. The first and second extensions directly oppose each other and the third and fourth extensions directly oppose each other. The actuation member is configured to be inserted into the driving member to transition the expandable spacer from a first configuration to a second configuration. The plurality of pins has a first and second pin, each of the first and second pins has a first end and a second end. The first end or the second end of each pin passes through and is received by one opening disposed on the main body, one opening disposed on the first endplate, one opening disposed on the second endplate, and one opening disposed on the driving member to assemble the main body, the first endplate, the second endplate, and the driving member together.

Additional understanding of the example expandable intervertebral spacers can be obtained by review of the detailed description, below, and the appended drawings.

DESCRIPTION OF SELECTED EXAMPLES

The following detailed description and the appended drawings describe and illustrate various example expandable spacers. The description and drawings are provided to enable one skilled in the art to make and use one or more example expandable spacers. They are not intended to limit the scope of the claims in any manner.

Figure 1:
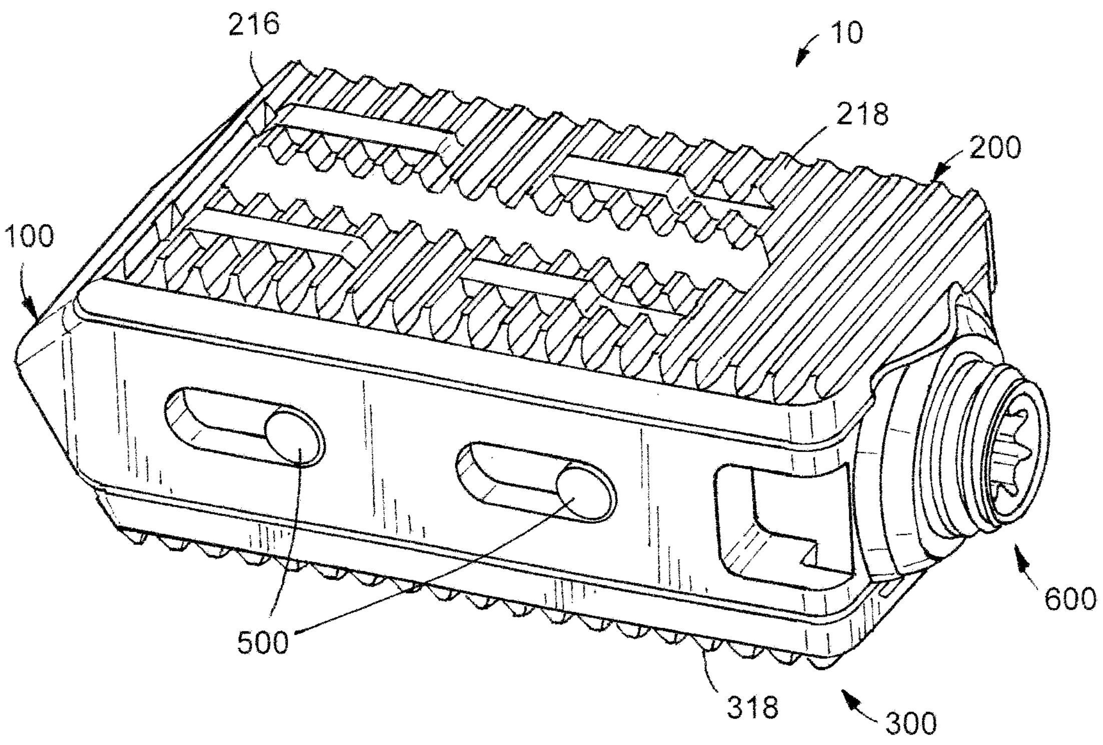
FIG. 1 is a perspective view of a first example expandable intervertebral spacer. The expandable spacer is shown in the first configuration.
Figure 2:
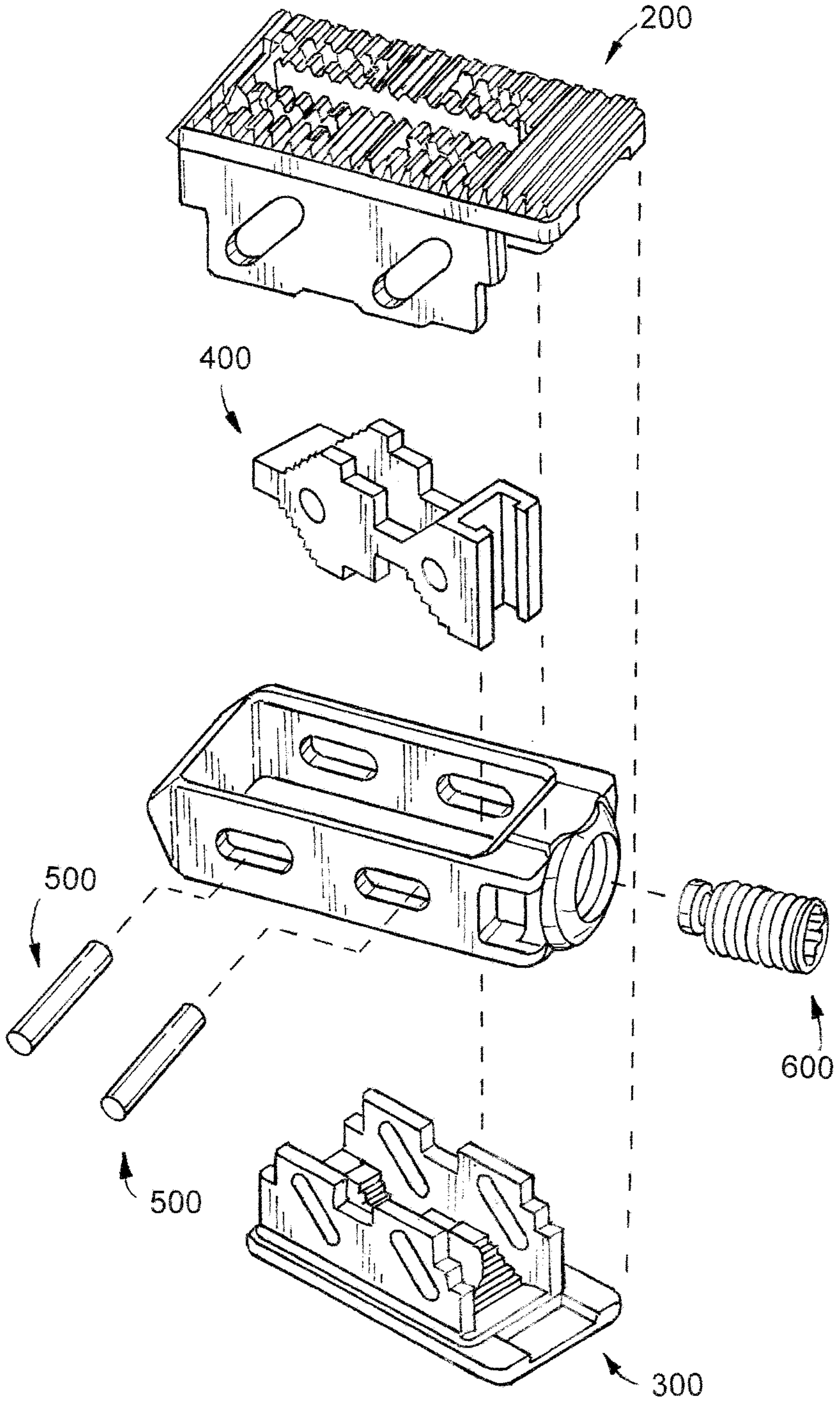
FIG. 2 is an exploded view of the first example expandable spacer illustrated in FIG. 1.
Figure 3:
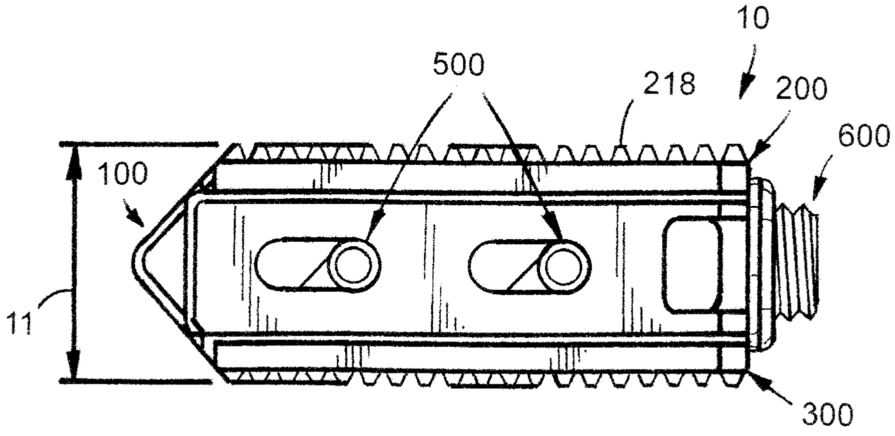
FIG. 3 is a side view of the first example expandable spacer. The expandable spacer is shown in the first configuration.
Figure 4:
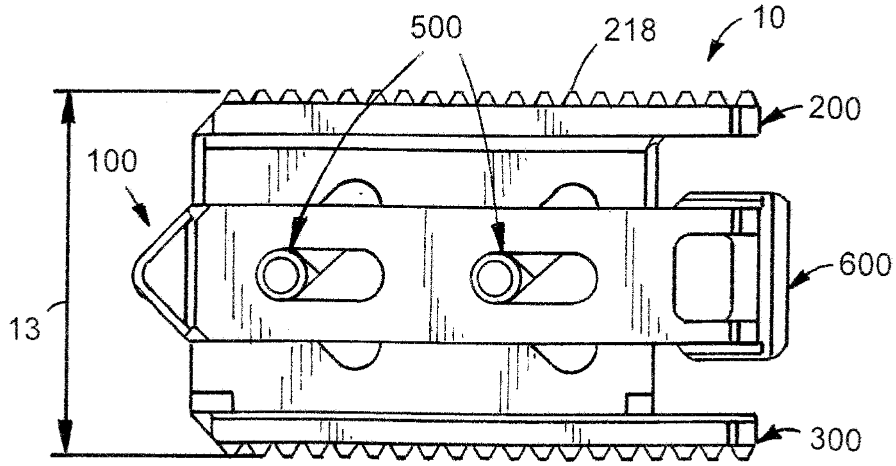
FIG. 4 is a side view of the first example expandable spacer. The expandable spacer is shown in the second configuration.
Figure 5:
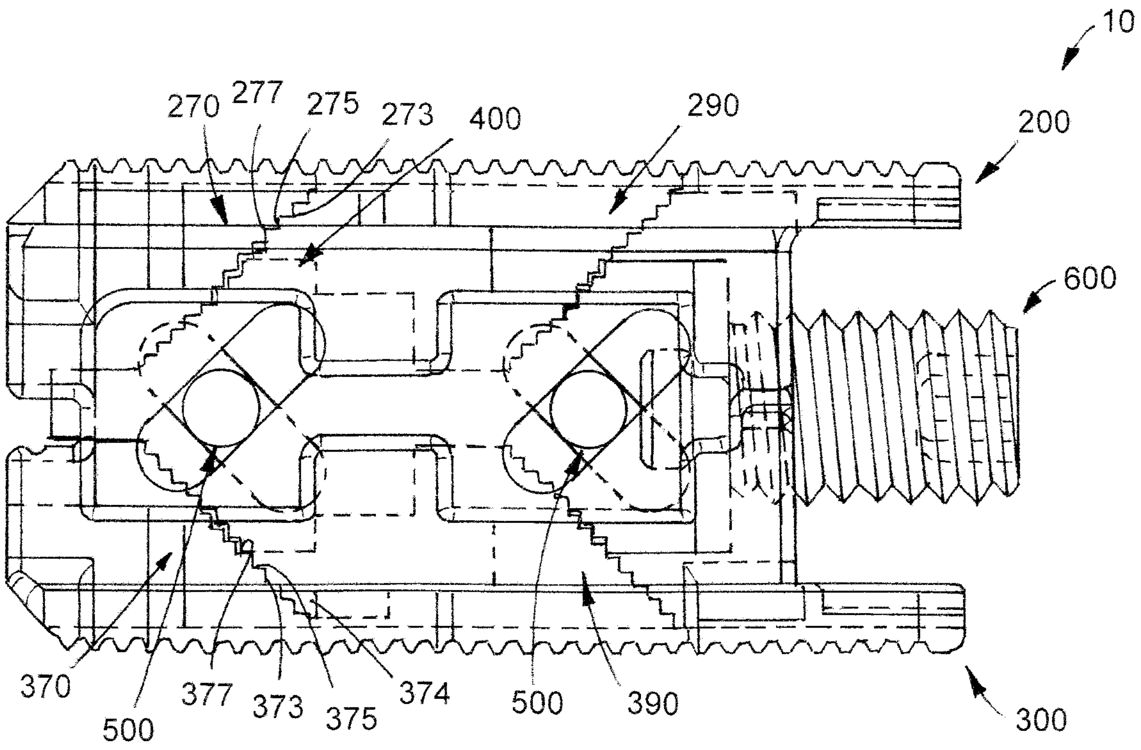
FIG. 5 is a side view of the first example expandable spacer. The expandable spacer is shown between the first configuration and the second configuration.
Figure 6:
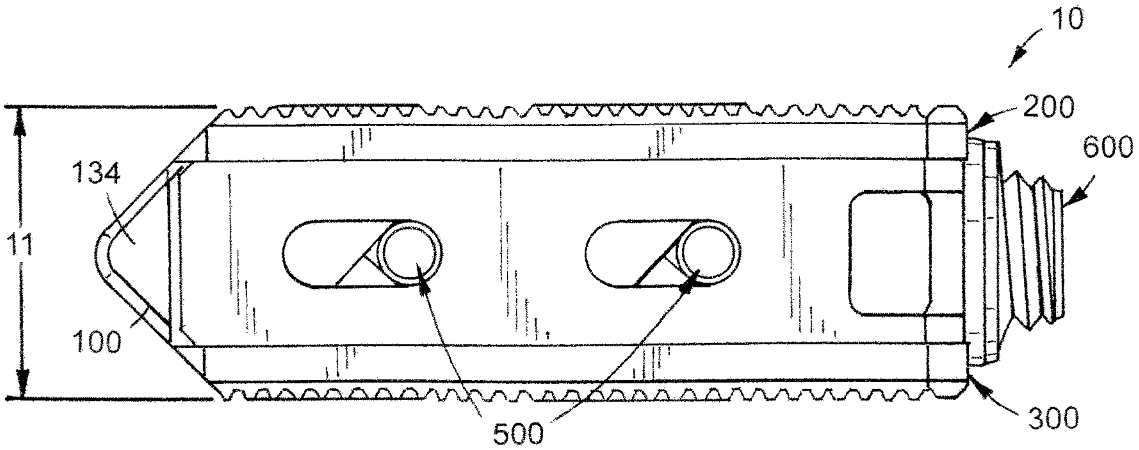
FIG. 6 is another side view of the first example expandable spacer illustrated in FIG. 1. The expandable spacer is shown in the first configuration.
Figure 7:
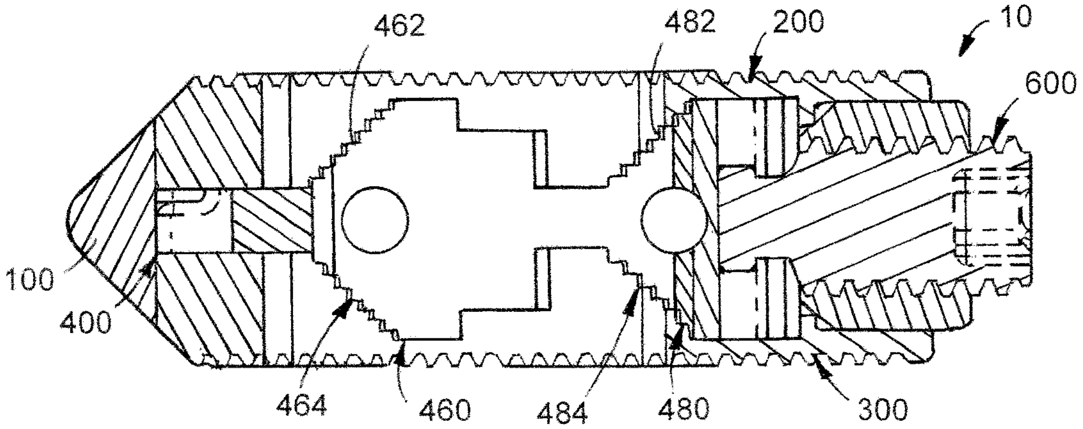
FIG. 7 is a sectional view of the first example expandable spacer illustrated in FIG. 6.

Each of FIGS. 1, 2, 3, 4, 5, 6, 7, 8, 9, 10, 11, 12, 13, 14, 15, 16, 17, 18, 19, 20, and 21 illustrates an example expandable spacer 10 or one or more components thereof. The expandable spacer 10 comprises a main body 100, a first endplate 200, a second endplate 300, a driving member 400, a plurality of pins 500, and an actuation member 600. The expandable spacer 10 is movable between a first configuration and a second configuration. In the first configuration, as illustrated in FIGS. 1, 3, and 6 each of the first endplate 200 and second endplate 300 interfaces with the main body 100. Also, each of the driving member 400, each pin of the plurality of pins 500, and the actuation member 600 is in a first position. In the second configuration, as illustrated in FIGS. 4 and 21, each of the first and second endplates 200, 300 is spaced such that the distance between the first and second endplates 200, 300 has increased as compared to the first configuration. The expandable spacer 10 moves between the first configuration and the second configuration through rotational movement of the actuation member 600, which forces the driving member 400 to move linearly along a longitudinal axis of the expandable spacer 10. This linear movement of the driving member 400 also moves each pin of the plurality of pins 500, which, as a result of their disposition in respective openings 230, 251, 330, 351 in the respective endplates 200, 300, forces the first and second endplates 200, 300 away from each other in opposing directions along an axis transverse to the longitudinal axis.

Figure 8:
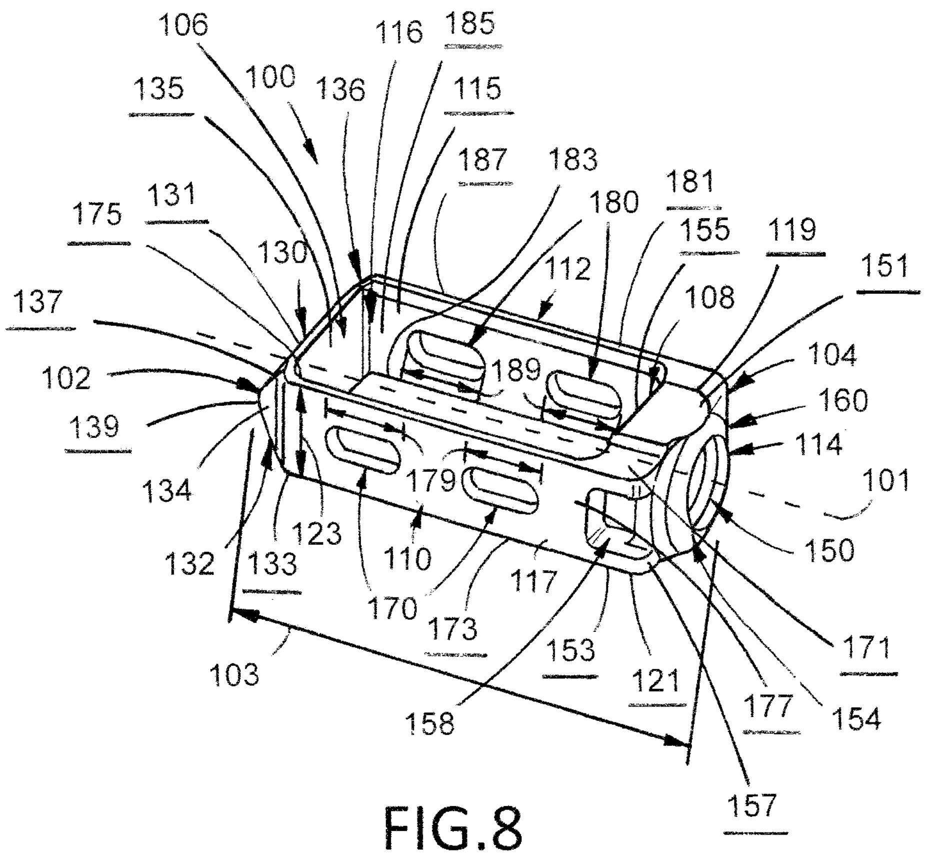
FIG. 8 is a perspective view of the main body of the first example expandable spacer illustrated in FIG. 1.

As shown in FIG. 8, the main body 100 has a main body first end 102, a main body second end 104, a lengthwise axis 101 extending between the main body first end 102 to the main body second end 104, a main body first lateral wall 106, a main body second lateral wall 108, a main body third lateral wall 110, a main body fourth lateral wall 112, a threaded opening 114, a main body inner surface 115, a main body outer surface 117, a main body top surface 119, and a main body bottom surface 121. The main body first lateral wall 106 has an upper surface 131, an opposing lower surface 133, an inner surface 135, and an opposing outer surface 137. The main body second lateral wall 108 has an upper surface 151, an opposing lower surface 153, an inner surface 155, and an opposing outer surface 157. The main body third lateral wall 110 has an upper surface 171, an opposing lower surface 173, an inner surface 175, and an opposing outer surface 177. The main body fourth lateral wall 112 has an upper surface 181, an opposing lower surface 183, an inner surface 185, and an opposing outer surface 187. The inner surfaces 135, 155, 175, 185 of the main body first lateral wall 106, main body second lateral wall 108, main body third lateral wall 110, and main body fourth lateral wall 112 cooperatively define a main body interior chamber 116. Similarly, the opposing outer surfaces 137, 157, 177, 187 of the main body first lateral wall 106, main body second lateral wall 108, main body third lateral wall 110, and main body fourth lateral wall 112 cooperatively define the main body outer surface 117. The upper surfaces 131, 151, 171, 181 of the main body first lateral wall 106, main body second lateral wall 108, main body third lateral wall 110, and main body fourth lateral wall 112 cooperatively define the main body top surface 119. Similarly, the opposing lower surfaces 133, 153, 175, 185 of the main body first lateral wall 106, main body second lateral wall 108, main body third lateral wall 110, and main body fourth lateral wall 112 cooperatively define a main body bottom surface 121. Additionally, the main body 100 has a length 103 that is measured from the main body first end 102 to the main body second end 104.

The main body first end 102 defines the main body first lateral wall 106, a first angled portion 130, a second angled portion 132, a third angled portion 134, and a fourth angled portion 136. Each of the first, second, third, and fourth angled portions 130, 132, 134, 136 extends from the main body first lateral wall 106 to the main body first end 102 to define a rounded curvilinear edge 139 at the main body first end 102. The first angled portion 130 is measured at a first angle relative to the lengthwise axis 101 of the main body 100 and the second angled portion 132 is measured at a second angle relative to lengthwise axis 101 of the main body 100. In the illustrated embodiment, the first and second angles of the first and second angled portions 130, 132 are the same. While particular angles have been described for the first and second angled portions 130, 132, first and second angled portions may define any suitable first and second angles. Selection of suitable first and second angles for first and second angled portions can be based on various considerations, including the actual and/or expected dimensions of the space between the vertebral bodies and/or the actual and/or expected dimensions of the intervertebral space. An example angle considered suitable for a first angle and a second angle includes an angle of about 45°. The third angled portion 134 is measured at a third angle relative to the lengthwise axis 101 of the main body 100 and the fourth angled portion 136 is measured at a fourth angle relative to the lengthwise axis 101 of the main body 100. In the illustrated embodiment, the third and fourth angles of the third and fourth angled portions 134, 136 are the same. While particular angles have been described for the third and fourth angled portions 134, 136, third and fourth angled portions may define any suitable third and fourth angles. Selection of suitable third and fourth angles for third and fourth angled portions can be based on various considerations, including the actual and/or expected dimensions of the space between the vertebral bodies and/or the actual and/or expected dimensions of the intervertebral space. An example angle considered suitable for a third angle and a fourth angle includes an angle of about 45°.

As illustrated in FIG. 8, the main body second end 104 defines the main body second lateral wall 108, a threaded opening 114, a first recess 158, and a second recess 160. The threaded opening 114 has a threaded opening first end (not illustrated) and a threaded opening second end 154. The threaded opening first end is defined on the inner surface 155 of the main body second lateral wall 108 and the threaded opening second end 154 is disposed at the main body second end 104. The threaded opening 114 is sized and configured to mate with the thread 606 of the actuation member 600, which is described in detail below.

The first recess 158 is disposed on the main body third lateral wall 110 and the second recess 160 is disposed on the main body fourth lateral wall 112. The first recess 158 is defined between the main body top surface 119 and the main body bottom surface 121 and extends from the main body second end 104 to the main body interior chamber 116. The second recess 160 is defined between the main body top surface 119 and the main body bottom surface 121 and extends from the main body second end 104 to the main body interior chamber 116. In the illustrated embodiment, first and second recesses 156, 158 are equal in size, shape, and configuration. In addition, each of the first and second recesses 158, 160 are considered advantageous at least because the first and second recesses 158, 160 are sized and configured to receive an insertion instrument (not illustrated) to assist in inserting the expandable spacer 10 into an intervertebral space.

The main body third lateral wall 110 has a main body first set of openings 170, and the main body fourth lateral wall 112 has a main body second set of openings 180. Each opening of the main body first set of openings 170 extends through the main body third lateral wall 110 such that each opening extends from the main body inner surface 115 to the main body outer surface 117. Each opening of the main body second set of openings 180 extends through the main body fourth lateral wall 112 such that each opening extends between the main body inner surface 115 to the main body outer surface 117. In the illustrated embodiment, each opening of the main body first set of openings 170 is aligned with (e.g., coaxial with) an opening of the main body second set of openings 180 on the main body fourth lateral wall 112 such that each opening of the main body first set of openings 170 directly opposes an opening of the main body second set of openings 180. Each opening of the main body first set of openings 170 and the main body second set of openings 180 is sized and configured to receive a pin from a plurality of pins 500, which is described in detail below. The alignment and the configuration of each opening of the main body first and second set of openings 170, 180 because it provides a mechanism for a pin from the plurality of pins 500 to pass through an opening of the first set of openings 170 and an opening of the second set of openings 180 to connect and link the main body 100, the first endplate 200, the second endplate 300, and the driving member 400 together in order for the expandable spacer 10 to move between the first configuration to the second configuration. Each opening of the main body first set of openings 170 has a length 179 and each opening of the main body second set of openings has a length 189. The lengths 179,189 are measured between the main body first end 102 and the main body second end 104.

Each opening of the main body first and second set of openings 170, 180 can have any suitable size, shape, and configuration, and selection of a suitable size, shape, and/or configuration for an opening in a main body set of openings according to a particular embodiment can be based on various considerations, including the size of a pin passing through the openings, the overall height difference between the first configuration to the second configuration, and other considerations. Examples of structural configurations considered suitable for an opening defined by a main body include, but are not limited to, elongated shapes, and any other structural configuration considered suitable for a particular embodiment.

As illustrated in FIGS. 11, 12, 15, and 18 the first endplate 200 has a first endplate first end 202, a first endplate second end 204, a lengthwise axis 201 extending through the first endplate first end 202 and the first endplate second end 204, a first extension 206, a second extension 208, a first endplate top 209, and a first endplate bottom 211. The first endplate 200 has a length 203 that is measured from the first endplate first end 202 to the first endplate second end 204.

The first endplate top 209 defines a first endplate angled portion 216 that extends from the first endplate first end 202 toward the first endplate second end 204. When the expandable spacer 10 is in its first configuration, the first endplate angled portion 216 is aligned with the first angled portion 130 of the main body 100 such that the first endplate angled portion 216 lies on the same plane as the main body first angled portion 130. The first endplate top 209 also defines a set of protruding ridges 218 that extend between the first endplate angled portion 216 to the first endplate second end 204. The first endplate bottom 211 defines the first and second extensions 206, 208 and a first endplate bottom notch 220. The first endplate bottom notch 220 extends from the first endplate second end 204 and towards the first endplate first end 202. The first endplate bottom notch 220 is sized and configured to receive and interface with the portion of the main body that defines the threaded opening 114 when the expandable spacer 10 is in its first configuration.

The first extension 206 has a first extension first end 232 and a first extension second end 234. The second extension 208 has a second extension first end 252 and a second extension second end 254. In the illustrated embodiment, the first and second extensions 206, 208 of the first endplate 200 are disposed on the first endplate bottom 211, extend from the first endplate bottom and away from the first endplate top 209, and are parallel to each other. The first extension 206 includes a first set of openings 230 each of which is positioned at a first angle relative to a plane that is parallel to the lengthwise axis 201 of the first endplate 200. The second extension 208 includes a second set of openings 251 each of which is positioned at a second angle relative to a plane that is parallel to the lengthwise axis 201 of the first endplate 200. In the illustrated embodiment, each of the first and second angles are the same. While the first and second angles have been illustrated as being the same, the first and second angles can be any suitable angle and selection of a suitable angle can be based on various considerations, including the size of a pin passing through each opening, the overall height difference between the first configuration to the second configuration intended to be achieved, and other considerations. Examples of angles considered suitable include angles equal to about 45°. The first extension 206 includes a first extension inner surface 235 and a first extension outer surface 237. Each opening of the first set of openings 230 of the first extension 206 extends through the first extension 206 such that each opening extends from the first extension inner surface 235 to the first extension outer surface 237. The second extension 230 includes a second extension inner surface 255 and a second extension outer surface 257. Each opening of the second set of openings 251 of the second extension 208 extends through the second extension 208 such that each opening extends from the second extension inner surface 255 to the second extension outer surface 257.

Each opening of the first and second set of openings 230, 251 of the first and second extensions 206, 208 can have any suitable size, shape, and/or configuration and selection of a suitable size, shape, and/or configuration for an opening can be based on various considerations, including the size of a pin passing through the openings, the overall height difference between the first configuration to the second configuration intended to be achieved, and other considerations. Examples of suitable structural configurations for an opening include, but are not limited to, elongated shapes, and any other suitable structural configuration.

Figure 11:
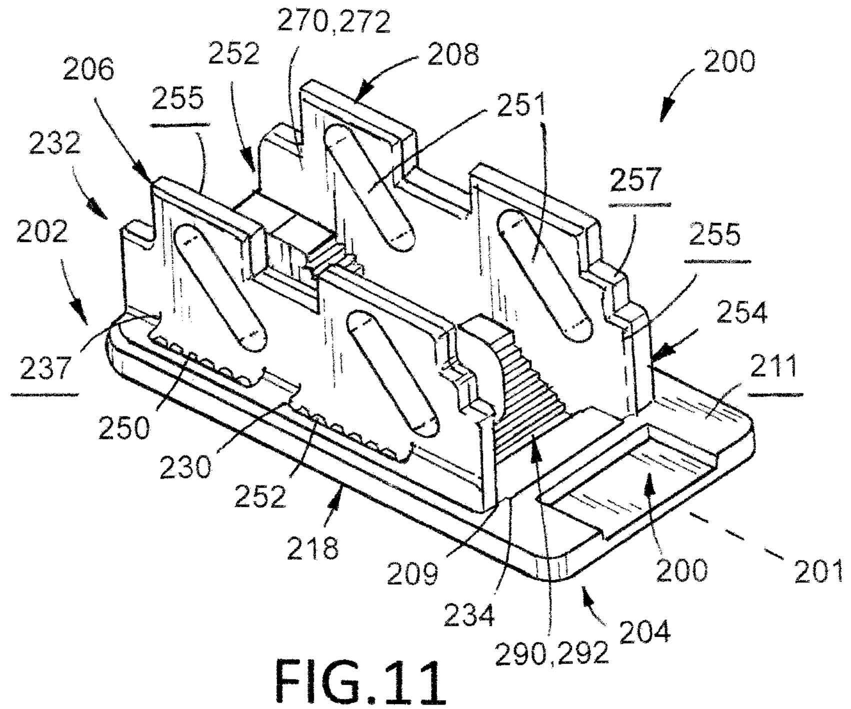
FIG. 11 is a perspective view of the first endplate of the first example expandable spacer illustrated in FIG. 1.
Figure 12:
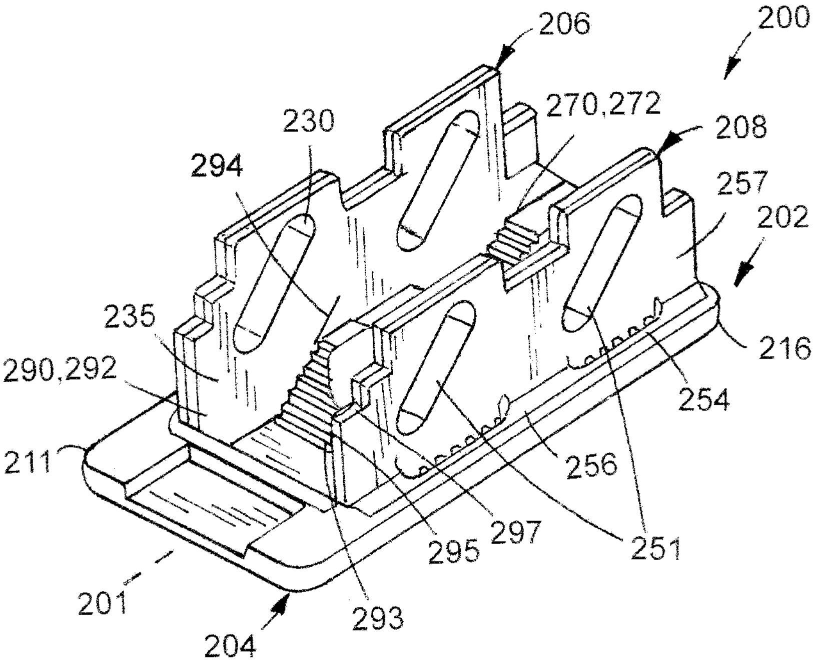
FIG. 12 is another perspective view of the first endplate of the first example expandable spacer illustrated in FIG. 1.
Figure 15:
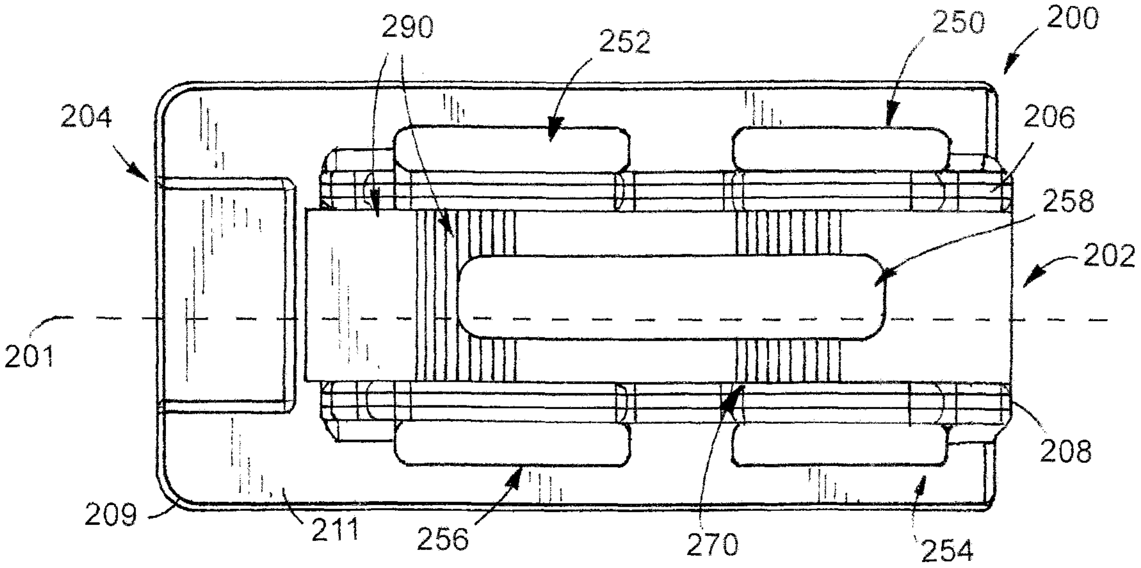
FIG. 15 is a bottom view of the first endplate of the first example expandable spacer illustrated in FIG. 1.

The first endplate 200 has a first protruding member 270 and a second protruding member 290. As illustrated in FIGS. 11, 12, and 15 the first protruding member 270 is disposed on the first endplate bottom 211, extends from the first endplate bottom 211 and away from the first endplate top 209, is positioned between the first endplate first end 202 and the second protruding member 290, and extends from the first extension 206 to the second extension 208. The second protruding member 290 is disposed on the first endplate bottom 211, extends from the first endplate bottom 211 and away from the first endplate top 209, is positioned between the first protruding member and the first endplate second end 204, and extends from the first extension 206 to the second extension 208. When assembled, the first protruding member 270 interfaces with the first and second extensions 460, 470 of the driving member 400 and the second protruding member 290 interfaces with the third and fourth extensions 480, 490 of the driving member 400 such that the expandable spacer 10 can move between its first and second configurations.

The first protruding member 270 defines a first plurality of steps 272 and the second protruding member 290 defines a second plurality of steps 292. As shown in FIG. 21, each step of the first set of plurality of steps 272 defines a step first surface 273, a step second surface 275, and a step faceted surface 277 (e.g., step intermediate portion). The step first surface 273 and the step second surface 275 of each step of the first set of plurality of steps 272 cooperatively define a slope 264 that extends between each step faceted surface 277 in the first set of plurality of steps 272. Each step of the second set of plurality of steps 292 defines a step first surface 293, a step second surface 295, and a step faceted surface 297 (e.g., step intermediate portion). The step first surface 293 has the same structural configuration as the step first surface 273. The step second surface 295 has the same structural configuration as the step second surface 275. The step faceted surface 297 has the same structural configuration as the step faceted surface 277. The step first surface 293 and the step second surface 295 of each step of the second set of plurality of steps 292 cooperatively define a slope 294 that extends between each step faceted surface 297 in the second set of plurality of steps 292. Selection of a suitable slope for each of the first and second sets of the plurality of steps 272, 292 can be based on various considerations, including the structural arrangement of a driving member. Examples of slopes include slopes equal to, less than, greater than, or about 15 degrees, 30 degrees, 45 degrees, 60 degrees, 75 degrees, between about 15 degrees and about 75 degrees, between about 30 degrees and about 45 degrees, and any other slope considered suitable for a particular embodiment.

Figure 18:
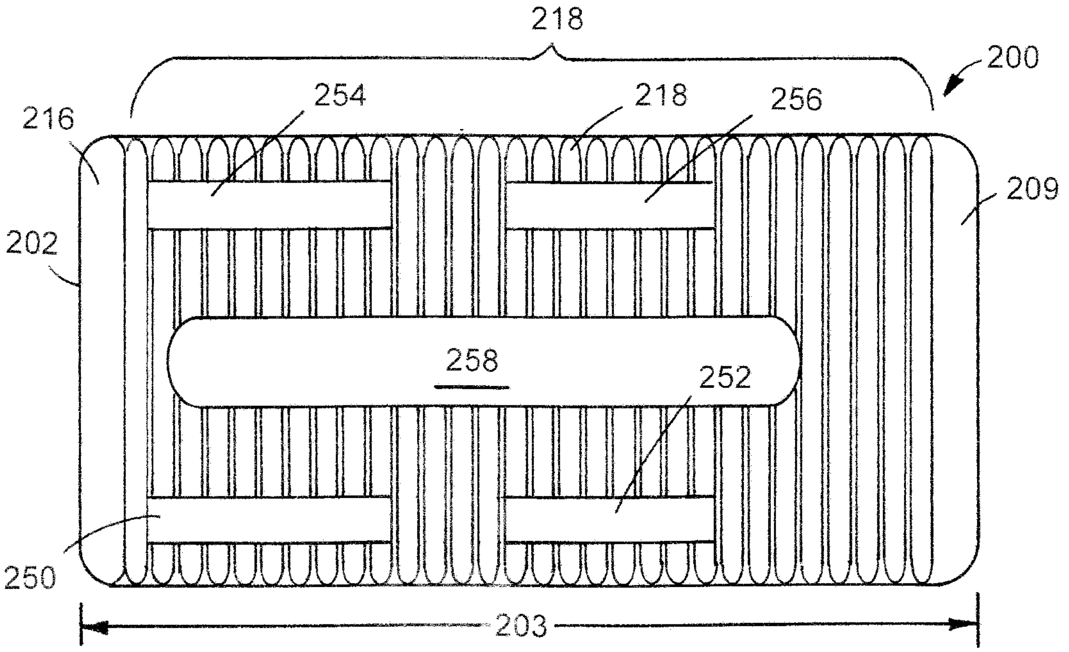
FIG. 18 is a top view of the first endplate of the first example expandable spacer illustrated in FIG. 1.

As shown in FIGS. 15 and 18, the first endplate 200 has a first slot 250, a second slot 252, a third slot 254, a fourth slot 256, and a fifth slot 258. Each of the first, second, third, fourth, and fifth slots 250, 252, 254, 256, 258 is elongated, has an axis that is disposed parallel to the lengthwise axis 201 of the first endplate 200, and extends through the entirety of the first endplate 200 such that each of the first, second, third, fourth, and fifth slots 250, 252, 254, 256, 258 extends from the first endplate top 209 to the first endplate bottom 211. As illustrated in FIGS. 15 and 18, the first slot 250 is disposed between the first extension 206 and an outer surface of the first endplate 200 and between the first endplate first end 202 and the second slot 252. The second slot 252 is disposed between the first extension 208 and an outer surface of the first endplate 200 and between the first slot 250 and the first endplate second end 204. The third slot 254 is disposed between the second extension 208 and an outer surface of the first endplate 200 and between the first endplate first end 202 and the fourth slot 256. The fourth slot 256 is disposed between the second extension 208 and an outer surface of the first endplate 200 and between the third slot 254 the first endplate second end 204. The fifth slot 258 is disposed between the first and second extensions 206, 208.

As illustrated in FIGS. 13, 14, 16, and 17 the second endplate 300 has a second endplate first end 302, a second endplate second end 304, a lengthwise axis 301 extending through the second endplate first end 302 and the second endplate second end 304, a third extension 306, a fourth extension 308, a second endplate top 309, and a second endplate bottom 311. The second endplate 300 has a length 303 that is measured from the second endplate first end 302 to the second endplate second end 304.

The second endplate top 309 defines a second endplate angled portion 316 that extends from second endplate first end 302 towards the second endplate second end 304. When the expandable spacer 10 is in its first configuration, the second endplate angled portion 316 is aligned with the second angled portion 132 of the main body 100 such that the second endplate angled portion 316 lies on the same plane as the second angled portion 132. The second endplate top 309 also defines a set of protruding ridges 318 that extend between the second endplate angled portion 316 to the second endplate second end 304. The second endplate bottom 311 defines the third and fourth extensions 306, 308 and a second endplate bottom notch 320. The second endplate bottom notch 320 extends from the second endplate second end 304 and towards the second endplate first end 302. The second endplate bottom notch 320 is sized and configured to receive and interface with threaded opening 114 when the expandable spacer 10 is in its first configuration.

The third extension 306 has a third extension first end 332 and a third extension second end 334. The fourth extension 308 has a fourth extension first end 352 and a fourth extension second end 354. In the illustrated embodiment, the third and fourth extensions 306, 308 of the second endplate 300 are disposed on the second endplate bottom 311, extends from the second endplate bottom and away from the second endplate top 309, and are parallel to each other. The third extension 306 includes a third set of openings 330 each of which is positioned at a third angle relative to a plane that is parallel to the lengthwise axis 301 of the second endplate 300. The fourth extension 308 includes a fourth set of openings 351 each of which is positioned at a fourth angle relative to a plane that is parallel to the lengthwise axis 301 of the second endplate 300. In the illustrated embodiment, each of the third and fourth angles are the same. While the third and fourth angles have been illustrated as being the same, the third and fourth angles can be any suitable angle and selection of a suitable angle can be based on various considerations, including the size of a pin passing through each opening, the overall height difference between the first configuration to the second configuration intended to be achieved, and other considerations. Examples of angles considered suitable include angles equal to about 45°. The third extension 306 includes a third extension inner surface 335 and a third extension outer surface 337. Each opening of the third set of openings 330 of the third extension 306 extends through the third extension 306 such that each opening extends from the third extension inner surface 335 to the third extension outer surface 337. The fourth extension 308 includes a fourth extension inner surface 355 and a fourth extension outer surface 357. Each opening of the fourth set of openings 351 of the fourth extension 308 extends through the fourth extension 308 such that each opening extends from the fourth extension inner surface 355 to the fourth extension outer surface 357.

Each opening of the third and fourth set of openings 330, 351 of the third and fourth extensions 306, 308 can have any suitable size, shape, and/or configuration and selection of a suitable size, shape, and/or configuration for an opening can be based on various considerations, including the size of a pin passing through the openings, the overall height difference between the first configuration to the second configuration intended to be achieved, and other considerations. Examples of suitable structural configurations for an opening include, but are not limited to, elongated shapes, and any other suitable structural configuration.

Figure 13:
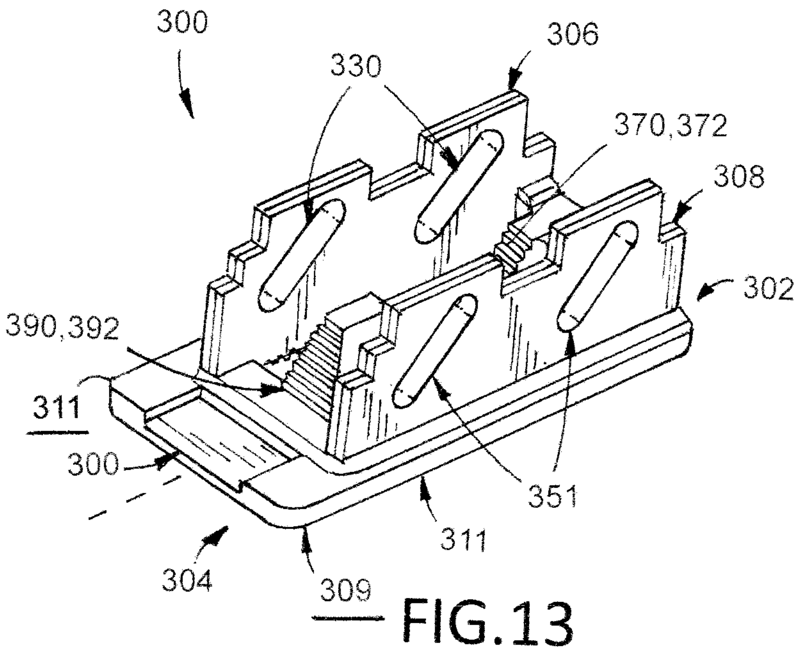
FIG. 13 is a perspective view of the second endplate of the first example expandable spacer illustrated in FIG. 1.
Figure 14:
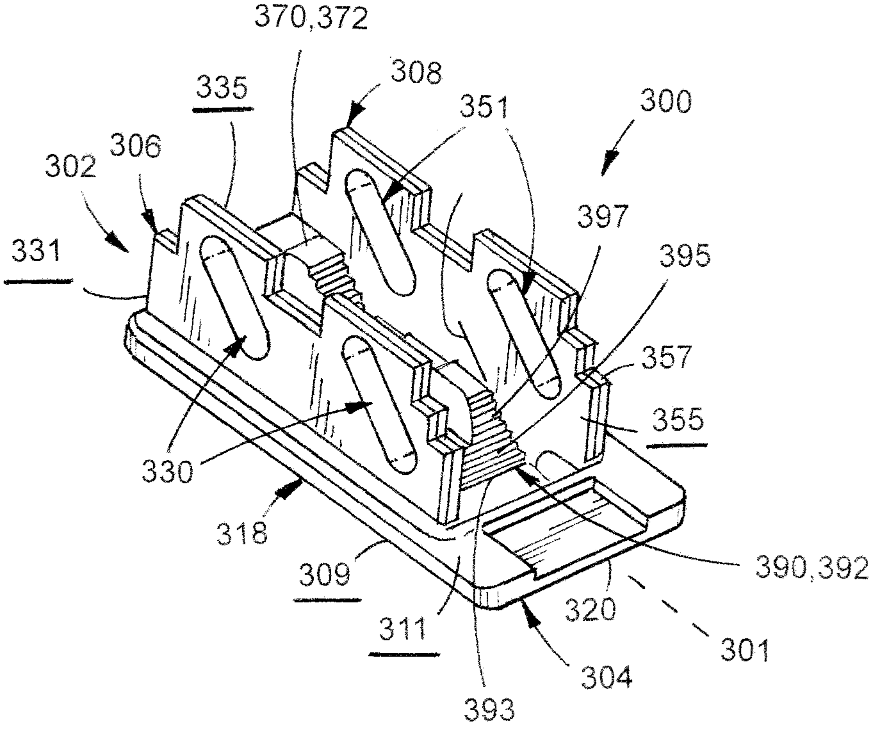
FIG. 14 is another perspective view of the second endplate of the first example expandable spacer illustrated in FIG. 1.
Figure 16:
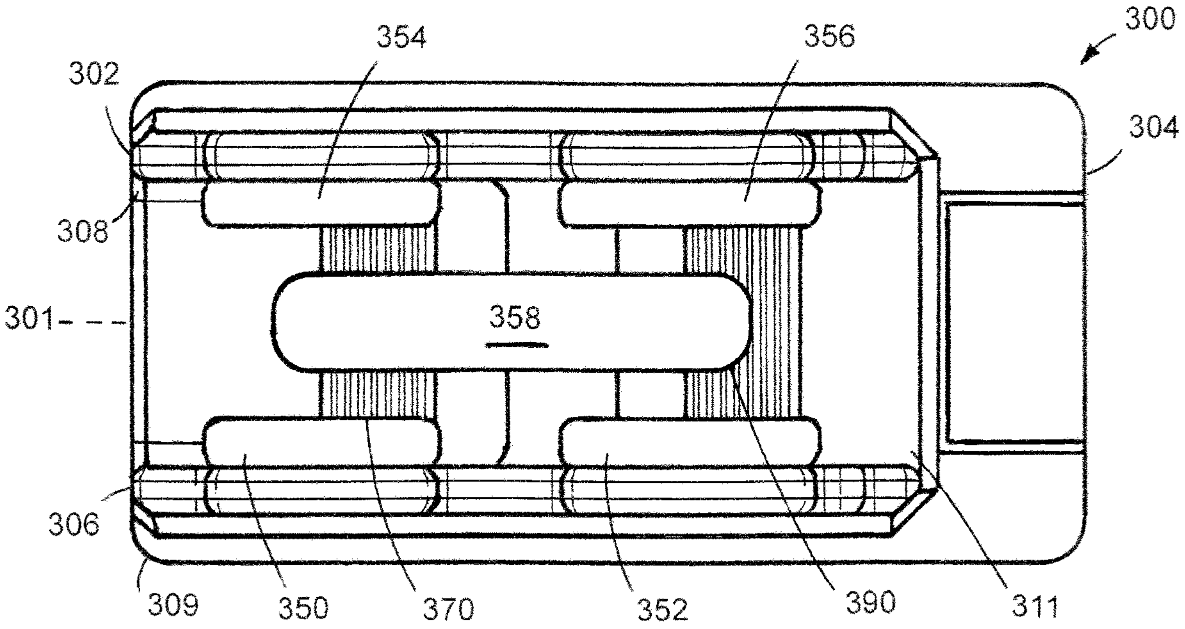
FIG. 16 is a bottom view of the second endplate of the first example expandable spacer illustrated in FIG. 1.

The second endplate 300 includes a third protruding member 370 and a fourth protruding member 390. As illustrated in FIGS. 13, 14, and 16, the third protruding member 370 is disposed on the second endplate bottom 311, extends from the second endplate bottom 311 and away from the second endplate top 309, is positioned between the second endplate first end 302 and the fourth protruding member 390, and between the sixth slot 350 and the third slot 354, as described in more detail herein. The fourth protruding member 390 is disposed on the second endplate bottom 311, extends from the second endplate bottom 311 and away from the second endplate top 309, is positioned between the first protruding member 370 and the second endplate second end 304, and between the second slot 352 and the fourth slot 356, as described in more detail herein. When assembled, the third protruding member 370 interfaces with the first and second extensions 460, 470 of the driving member 400 and the fourth protruding member 390 interfaces with the third and fourth extensions 480, 490 such that the expandable spacer 10 can move between its first and second configurations.

The third protruding member 370 defines a first plurality of steps 372 and the fourth protruding member 390 defines a second plurality of steps 392. The steps 372, 392 of the third and fourth protruding members 370, 390 of the second endplate 200 are similar to the steps defined by the first and second protruding members 270, 290 of the first endplate 200. As shown in FIG. 5, each step of the first plurality of steps 372 has a step first surface 373, and step second surface 375, and a faceted surface 377 (e.g., step intermediate portion). The step first surface 373 and the step second surface 375 of each step of the first set of plurality of steps 372 cooperatively define a slope 374 that extends between each step faceted surface 377 in the first set of plurality of steps 372. Each step of the second set of plurality of steps 392 defines a step first surface 393, a step second surface 395, and a step faceted surface 397 (e.g., step intermediate portion). The step first surface 393 has the same structural configuration as the step first surface 373. The step second surface 395 has the same structural configuration as the step second surface 375. The step faceted surface 397 has the same structural configuration as the step faceted surface 377. The step first surface 393 and the step second surface 395 of each step of the second set of plurality of steps 392 cooperatively define a slope 391 that extends between each step faceted surface 397 in the second set of plurality of steps 392. Selection of a suitable slope for each of the first and second sets of the plurality of steps 372, 392 can be based on various considerations, including the structural arrangement of a driving member. Examples of slopes include slopes equal to, less than, greater than, or about 15 degrees, 30 degrees, 45 degrees, 60 degrees, 75 degrees, between about 15 degrees and about 75 degrees, between about 30 degrees and about 45 degrees, and any other slope considered suitable for a particular embodiment.

Figure 17:
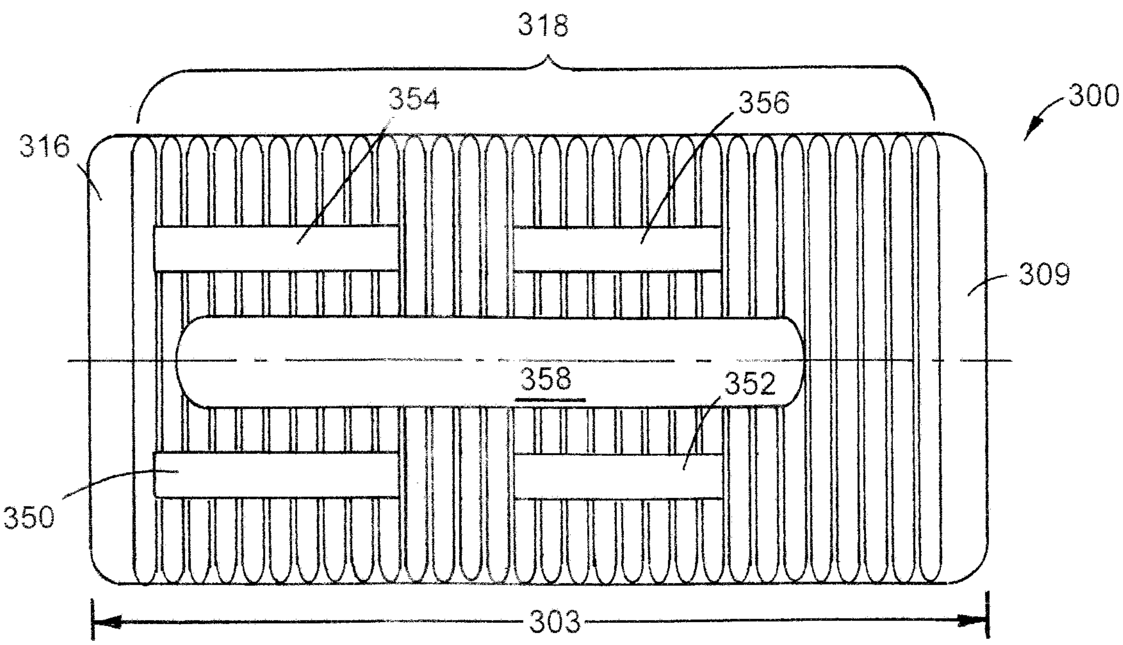
FIG. 17 is a top view of the second endplate of the first example expandable spacer illustrated in FIG. 1.

As shown in FIGS. 16 and 17, the second endplate 300 has a sixth slot 350, a seventh slot 352, an eighth slot 354, a ninth slot 356, and a tenth slot 358. Each of the sixth, seventh, eighth, ninth, and tenth slots 350, 352, 354, 356, 358 is elongated, has an axis that is disposed parallel to the lengthwise axis 301 of the second endplate 300, and extends through the entirety of the second endplate 300 such that each of the sixth, seventh, eighth, ninth, and tenth slots 350, 352, 354, 356, 358 extends from the second endplate top 309 to the second endplate bottom 311. As illustrated in FIGS. 16 and 17, the sixth slot 350 is disposed between the third and fourth extensions 306, 308 and between the second endplate first end 302 and the seventh slot 352. The seventh slot 352 is disposed between the third and fourth extensions 306, 308 and between the sixth slot 350 and the second endplate second end 304. The eighth slot 354 is disposed between the third and fourth extensions 306, 308 and between the second endplate first end 302 and the ninth slot 356. The ninth slot 356 is disposed between the third and fourth extensions 306, 308 and between the eighth slot 354 and the second endplate second end 304. The tenth slot 358 is disposed between the third and fourth extensions 306, 308, between the sixth slot 350 and the eighth slot 354, and between the seventh slot 352 and the ninth slot 356.

Figure 19:
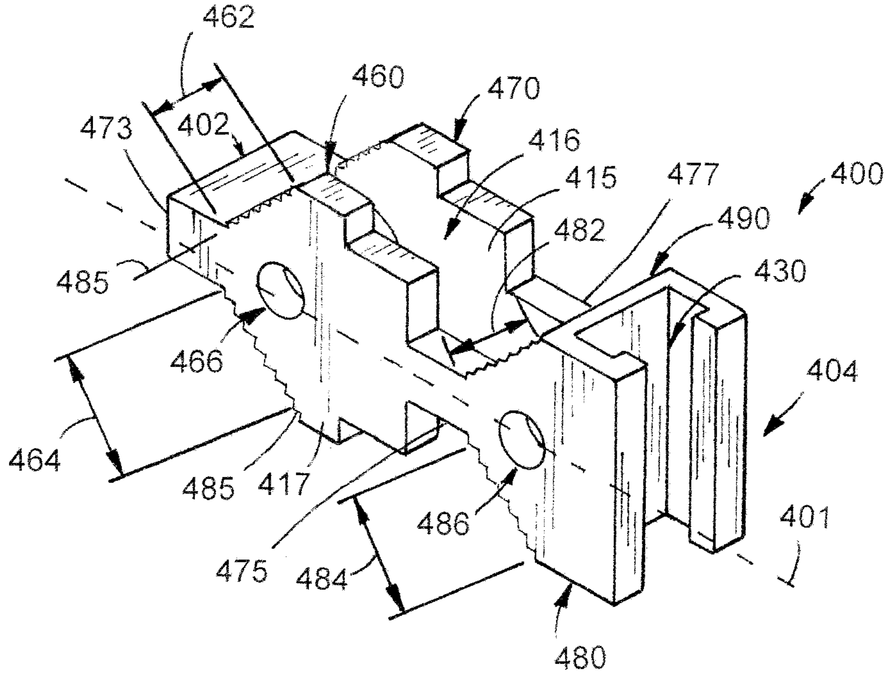
FIG. 19 is a perspective view of the driving member of the first example expandable spacer illustrated in FIG. 1.
Figure 20:
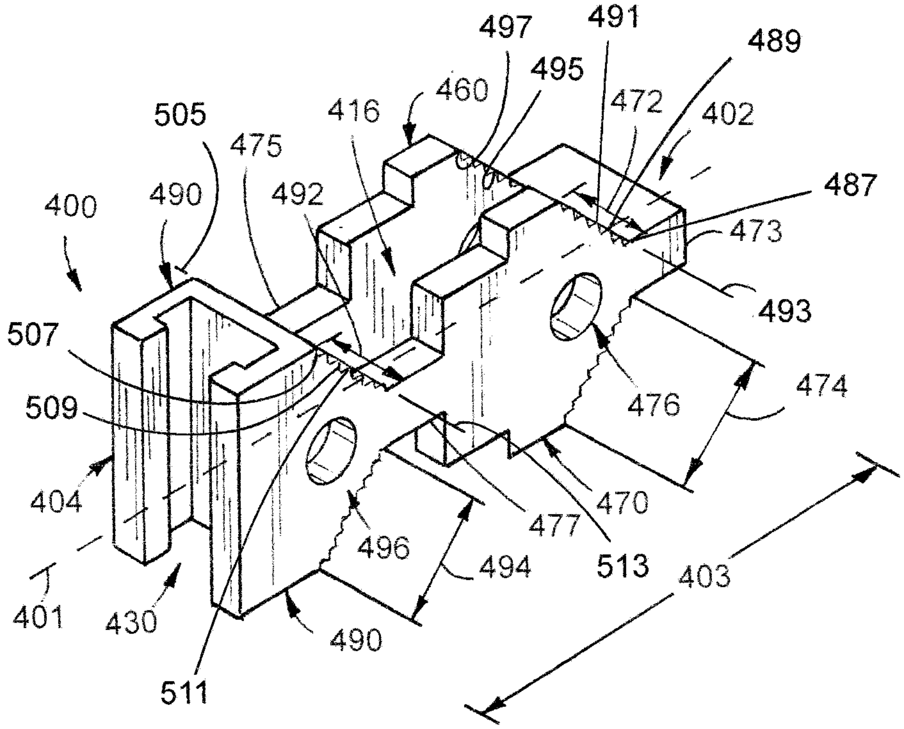
FIG. 20 is another perspective view of the driving member of the first example expandable spacer illustrated in FIG. 1.
Figure 21:
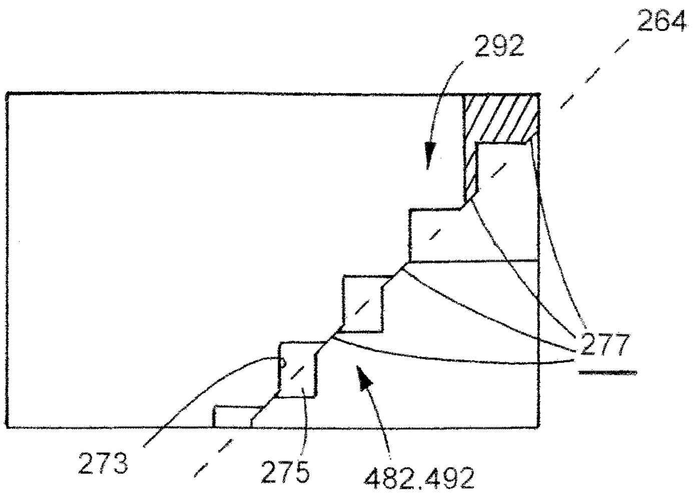
FIG. 21 is a partial sectional view of the first example expandable spacer illustrated in FIG. 1. The expandable spacer is shown between the first configuration and the second configuration.

As illustrated in FIGS. 19 and 20, the driving member 400 has a driving member first end 402, a driving member second end 404, a lengthwise axis 401 extending through the driving member first end 402 and the driving member second end 404, a driving member interior surface 415, a driving member interior chamber 416, and a driving member outer surface 417. The driving member 400 has a length 403 that is measured from the driving member first end 402 to the driving member second end 404. The driving member 400 has a first position when the expandable spacer 10 is in the first configuration. The driving member 400 has a second position when the expandable spacer 10 is in the second configuration.

The driving member second end 404 defines a driving member channel 430 that extends along an axis that is perpendicular to the lengthwise axis 401 of the driving member 400. The driving member channel 430 and the driving member interior chamber 416 are separated and are not in fluid communication with one another. The driving member channel 430 is sized and configured to mate with the cam 608 of the actuation member 600, as described in detail herein, to allow the expandable spacer 10 to transition from the first configuration to the second configuration when the actuation member 600 is moved towards the driving member interior chamber 416.

The driving member 400 has a driving member first extension 460, a driving member second extension 470, a driving member third extension 480, and a driving member fourth extension 490. In the illustrated embodiment, the driving member first extension 460 is disposed between the driving member first end 402 and the driving member 400 third extension 480, the driving member second extension 470 is disposed between the driving member first end 402 and the driving member 400 fourth extension 490, the driving member third extension 480 is disposed between the driving member first extension 460 and the driving member second end 404, and the driving member fourth extension 490 is disposed between the driving member second extension 470 and the driving member second end 404. The driving member first extension 460 is parallel to the driving member second extension 470 and the driving member third extension 480 is parallel to the driving member fourth extension 490.

In the illustrated embodiment, the driving member first extension 460 defines a first opening 466, the second extension 470 defines a second opening 476, the third extension 480 defines a third opening 486, and the fourth extension defines a fourth opening 496. Each of the openings 466, 476, 486, 496 extends from a driving member inner surface to the driving member outer surface. In the illustrated embodiment, the opening 466 is coaxial with opening 476 and opening 486 is coaxial with opening 496. Each of the openings 466, 476, 486, 496 is sized and configured to receive a pin of the plurality of pins 500, as described herein. The alignment and the configuration of each opening 466, 476, 486, 496 provides a mechanism to pass a pin of the plurality of pins 500 through two coaxial openings to connect the main body 100, the first endplate 200, the second endplate 300, and the driving member 400 together such that the expandable spacer 10 can move between the first configuration to the second configuration.

Each of the openings 466, 476, 486, 496 can have any suitable size, shape, and/or configuration, and selection of a suitable size, shape, and/or configuration for an opening can be based on various considerations, including the size of a pin passing through the opening, the overall height difference between the first configuration to the second configuration, and other considerations. Examples of suitable structural configurations include, but are not limited to, circular, elongated circular shapes, elongated rectangular shapes, ovoid, elliptical, and any other suitable structural configuration. In the illustrated embodiment, each opening 466, 576, 486, 496 has a circular shape.

As illustrated in FIGS. 19 and 20, the driving member first extension 460 has an upper set of steps 462 and a lower set of steps 464. The upper set of steps 462 extends from a driving member projection 473 to a driving member first elongate member 475. The lower set of steps 464 extends from the driving member projection 473 to the driving member first elongate member 475. The upper and lower sets of steps 462, 464 extend away from a plane that contains the lengthwise axis 401 of the driving member 400 in opposite directions. Each step of the upper set of steps 462 and the lower set of steps 464 defines a step first surface 479, a step second surface 481, and a step faceted surface 483 (e.g., step intermediate portion). The step first surface 479 of the upper set of steps 462 has the same structural configuration as the step first surface 273. The step second surface 481 upper set of steps 462 has the same structural configuration as the step second surface 275. The step faceted surface 483 upper set of steps 462 has the same structural configuration as the step faceted surface 277. The step first surface 479 of the lower set of steps 464 has the same structural configuration as the step first surface 373. The step second surface 481 lower set of steps 464 has the same structural configuration as the step second surface 375. The step faceted surface 483 of the lower set of steps 464 has the same structural configuration as the step faceted surface 377. The step first surface 479 and the step second surface 481 cooperatively define a slope 485 that extends between each step faceted surface 483. Selection of a suitable slope can be based on various considerations, including the structural arrangement of a driving member. Examples of slopes include slopes equal to, less than, greater than, or about 15 degrees, 30 degrees, 45 degrees, 60 degrees, 75 degrees, between about 15 degrees and about 75 degrees, between about 30 degrees and about 45 degrees, and any other slope considered suitable for a particular embodiment.

The upper set of steps 462 is configured to mate with and interact with the first set of plurality of steps 272 of the first protruding member 270 of the first endplate 200. The lower sets of steps 464 is configured to mate with and interact with the first plurality of steps 372 of the third protruding member 370 of the second endplate 300. Thus, once the expandable spacer 10 is assembled, the upper set of steps 462 of the driving member first extension 460 interfaces with the first set of plurality of steps 272 of the first protruding member 270 when the expandable spacer 10 transitions from a first configuration to a second configuration, and the lower set of steps 464 of the driving member first extension 460 interfaces with the first plurality of steps 372 of the third protruding member 370 when the expandable spacer 10 transitions from a first configuration to a second configuration. The interaction between the upper and lower sets of steps 462, 464 of the driving member first extension 460 and the first and third sets of plurality of steps 272, 372 of the first and third protruding members provides a mechanism for providing continuous movement between the driving member 400 and the first and second endplates 200, 300 during transition, allows for an smooth transition between one step and another relative to devices that do not include faceted surfaces, and allows for fixation once transition is complete and the expandable spacer 10 is under load. When in the expandable spacer 10 is in the first or second configuration, the step first surface 479 of the upper set of steps 462 contacts the step first surface 273, the step second surface 481 of the upper set of steps 462 contacts the step second surface 275, the step first surface 479 of the lower set of steps 464 contact the step first surface 373, and the step second surface 481 of the lower set of steps 464 contacts the step second surface 375. When moving between the first and second configurations, the step faceted surface 483 of the upper set of steps 462 contacts the step faceted surface 277 and the step faceted surface 483 of the lower set of steps 462 contacts the step faceted surface 377.

As illustrated in FIGS. 19 and 20, the driving member second extension 470 has an upper set of steps 472 and a lower set of steps 474. The upper set of steps 472 extends from the driving member projection 473 to the driving member second elongate member 477. The lower set of steps 474 extends from the driving member projection 473 to the driving member second elongate member 477. The upper and lower sets of steps 472, 474 extend away from a plane that contains the lengthwise axis 401 of the driving member 400 is opposite directions. Each step of the upper set of steps 472 and the lower set of steps 474 defines a step first surface 487, a step second surface 489, and a step faceted surface 491 (e.g., step intermediate portion). The step first surface 487 of the upper set of steps 472 has the same structural configuration as the step first surface 273. The step second surface 489 upper set of steps 472 has the same structural configuration as the step second surface 275. The step faceted surface 491 upper set of steps 472 has the same structural configuration as the step faceted surface 277. The step first surface 487 of the lower set of steps 474 has the same structural configuration as the step first surface 373. The step second surface 489 lower set of steps 474 has the same structural configuration as the step second surface 375. The step faceted surface 491 lower set of steps 474 has the same structural configuration as the step faceted surface 377. The step first surface 487 and the step second surface 489 cooperatively define a slope 493 that extends between each step faceted surface 491. Selection of a suitable slope can be based on various considerations, including the structural arrangement of a driving member. Examples of slopes include slopes equal to, less than, greater than, or about 15 degrees, 30 degrees, 45 degrees, 60 degrees, 75 degrees, between about 15 degrees and about 75 degrees, between about 30 degrees and about 45 degrees, and any other slope considered suitable for a particular embodiment.

The upper set of steps 472 is configured to mate with and interact with the first set of plurality of steps 272 of the first protruding member 270 of the first endplate 200. The lower sets of steps 474 is configured to mate with and interact with the first plurality of steps 372 of the third protruding member 370 of the second endplate 300. Thus, once the expandable spacer 10 is assembled, the upper set of steps 472 of the driving member second extension 470 interfaces with the first set of plurality of steps 272 of the first protruding member 270 when the expandable spacer 10 transitions from a first configuration to a second configuration, and the lower set of steps 474 of the driving member second extension 470 interfaces with the first plurality of steps 372 of the third protruding member 370 when the expandable spacer 10 transitions from a first configuration to a second configuration. The interaction between the upper and lower sets of steps 472, 474 of the driving member second extension 470 and the first and third sets of plurality of steps 272, 372 of the first and third protruding members provides a mechanism for providing continuous movement between the driving member 400 and the first and second endplates 200, 300 during transition, allows for an smooth transition between one step and another relative to devices that do not include faceted surfaces, and allows for fixation once transition is complete and the expandable spacer 10 is under load. When in the expandable spacer 10 is in the first or second configuration, the step first surface 487 of the upper set of steps 472 contacts the step first surface 273, the step second surface 489 of the upper set of steps 472 contacts the step second surface 275, the step first surface 487 of the lower set of steps 474 contact the step first surface 373, and the step second surface 489 of the lower set of steps 474 contacts the step second surface 375. When moving between the first and second configurations, the step faceted surface 491 of the upper set of steps 472 contacts the step faceted surface 277 and the step faceted surface 491 of the lower set of steps 474 contacts the step faceted surface 377.

As illustrated in FIGS. 19 and 20, the driving member third extension 480 has an upper set of steps 482 and a lower set of steps 484. The upper set of steps 482 extends from the driving member first elongate member 475 to the portion of the driving member 400 that defines the channel 430. The lower set of steps 484 extends from the driving member first elongate member 475 the portion of the driving member 400 that defines the channel 430. The upper and lower sets of steps 482, 484 extend away from a plane that contains the lengthwise axis 401 of the driving member 400 is opposite directions. Each step of the upper set of steps 482 and the lower set of steps 484 defines a step first surface 495, a step second surface 497, and a step faceted surface 499 (e.g., step intermediate portion). The step first surface 495 of the upper set of steps 482 has the same structural configuration as the step first surface 293. The step second surface 497 of the upper set of steps 482 has the same structural configuration as the step second surface 295. The step faceted surface 499 of the upper set of steps 482 has the same structural configuration as the step faceted surface 297. The step first surface 495 of the lower set of steps 484 has the same structural configuration as the step first surface 393. The step second surface 497 of the lower set of steps 484 has the same structural configuration as the step second surface 395. The step faceted surface 499 of the lower set of steps 484 has the same structural configuration as the step faceted surface 397. The step first surface 495 and the step second surface 497 cooperatively define a slope 505 that extends between each step faceted surface 499. Selection of a suitable slope can be based on various considerations, including the structural arrangement of a driving member. Examples of slopes include slopes equal to, less than, greater than, or about 15 degrees, 30 degrees, 45 degrees, 60 degrees, 75 degrees, between about 15 degrees and about 75 degrees, between about 30 degrees and about 45 degrees, and any other slope considered suitable for a particular embodiment.

The upper set of steps 482 is configured to mate with and interact with the second plurality of steps 292 of the first endplate 200. The lower sets of steps 484 is configured to mate with and interact with the second plurality of steps 392 of the second endplate 300. Thus, once the expandable spacer 10 is assembled, the upper set of steps 482 interfaces with the second plurality of steps 292 when the expandable spacer 10 transitions from a first configuration to a second configuration, and the lower set of steps 484 interfaces with the plurality of steps 392 when the expandable spacer 10 transitions from a first configuration to a second configuration. The interaction between the upper and lower sets of steps 482, 484 and the plurality of steps 292, 392 provides a mechanism for providing continuous movement between the driving member 400 and the first and second endplates 200, 300 during transition, allows for an smooth transition between one step and another relative to devices that do not include faceted surfaces, and allows for fixation once transition is complete and the expandable spacer 10 is under load. When in the expandable spacer 10 is in the first or second configuration, the step first surface 495 of the upper set of steps 482 contacts the step first surface 293, the step second surface 297 of the upper set of steps 482 contacts the step second surface 295, the step first surface 495 of the lower set of steps 484 contact the step first surface 393, and the step second surface 497 of the lower set of steps 484 contacts the step second surface 395. When moving between the first and second configurations, the step faceted surface 499 of the upper set of steps 482 contacts the step faceted surface 297 and the step faceted surface 499 of the lower set of steps 484 contacts the step faceted surface 397.

As illustrated in FIGS. 19 and 20, the driving member fourth extension 490 has an upper set of steps 492 and a lower set of steps 494. The upper set of steps 492 extends from the driving member second elongate member 477 to the portion of the driving member 400 that defines the channel 430. The lower set of steps 494 extends from the driving member second elongate member 477 the portion of the driving member 400 that defines the channel 430. The upper and lower sets of steps 492, 494 extend away from a plane that contains the lengthwise axis 401 of the driving member 400 is opposite directions. Each step of the upper set of steps 492 and the lower set of steps 494 defines a step first surface 507, a step second surface 509, and a step faceted surface 511 (e.g., step intermediate portion). The step first surface 507 of the upper set of steps 492 has the same structural configuration as the step first surface 293. The step second surface 509 of the upper set of steps 492 has the same structural configuration as the step second surface 295. The step faceted surface 511 of the upper set of steps 492 has the same structural configuration as the step faceted surface 297. The step first surface 507 of the lower set of steps 494 has the same structural configuration as the step first surface 393. The step second surface 509 of the lower set of steps 494 has the same structural configuration as the step second surface 395. The step faceted surface 511 of the lower set of steps 494 has the same structural configuration as the step faceted surface 397. The step first surface 507 and the step second surface 509 cooperatively define a slope 513 that extends between each step faceted surface 511. Selection of a suitable slope can be based on various considerations, including the structural arrangement of a driving member. Examples of slopes include slopes equal to, less than, greater than, or about 15 degrees, 30 degrees, 45 degrees, 60 degrees, 75 degrees, between about 15 degrees and about 75 degrees, between about 30 degrees and about 45 degrees, and any other slope considered suitable for a particular embodiment.

The upper set of steps 492 is configured to mate with and interact with the second plurality of steps 292 of the first endplate 200. The lower set of steps 494 is configured to mate with and interact with the second plurality of steps 392 of the second endplate 300. Thus, once the expandable spacer 10 is assembled, the upper set of steps 492 interfaces with the second plurality of steps 292 when the expandable spacer 10 transitions from a first configuration to a second configuration, and the lower set of steps 494 interfaces with the plurality of steps 392 when the expandable spacer 10 transitions from a first configuration to a second configuration. The interaction between the upper and lower sets of steps 492, 494 and the plurality of steps 292, 392 provides a mechanism for providing continuous movement between the driving member 400 and the first and second endplates 200, 300 during transition, allows for an smooth transition between one step and another relative to devices that do not include faceted surfaces, and allows for fixation once transition is complete and the expandable spacer 10 is under load. When in the expandable spacer 10 is in the first or second configuration, the step first surface 507 of the upper set of steps 492 contacts the step first surface 293, the step second surface 509 of the upper set of steps 492 contacts the step second surface 295, the step first surface 507 of the lower set of steps 494 contacts the step first surface 393, and the step second surface 509 of the lower set of steps 494 contacts the step second surface 395. When moving between the first and second configurations, the step faceted surface 511 of the upper set of steps 492 contacts the step faceted surface 297 and the step faceted surface 511 of the lower set of steps 494 contacts the step faceted surface 397.

Figure 9:
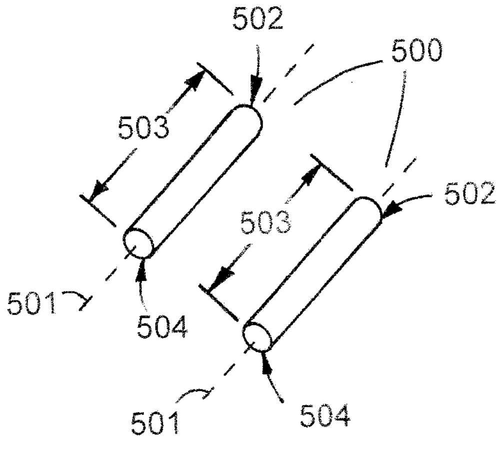
FIG. 9 is a perspective view of the plurality of pins of the first example expandable spacer illustrated in FIG. 1.

In the illustrated embodiment, as shown in FIG. 9, each pin of the plurality of pins 500 has a pin first end 502, a pin second end 504, a lengthwise axis 501 of each pin that extends from the pin first end 502 to the pin second end 504, and a length 503 that is measured from the pin first end 502 to the pin second end 504.

Each pin of the plurality of pins 500 can have any suitable size, shape, and/or configuration, and selection of a suitable size, shape, and/or configuration for a pin of an expandable spacer can be based on various considerations, including the size of the openings of the expandable spacer. Examples of cross-sectional shapes and configurations considered suitable for a pin include, but are not limited to, hexagonal, triangular, square, circular, ovoid, elliptical, or any other shape or configuration considered suitable for a particular application. In the illustrated embodiment, each pin of the plurality of pins 500 has a circular cross-sectional configuration. Any suitable number of pins can be included in an expandable spacer. Examples of numbers of pins considered suitable to include in an expandable spacer include one, a plurality, two, three, four, more than four, and any other number considered suitable for a particular embodiment.

In the illustrated embodiment, each pin of the plurality of pins 500 extends through the expandable spacer 10 such that each pin of the plurality of pins extends through the main body 100, the first endplate 200, the second endplate 300, and the driving member 400 when the expandable spacer 10 is assembled. In an alternative embodiment, each pin of the plurality of pins 500 does not extend entirely through the expandable spacer 10 and terminates into the driving member 400. In this alternative embodiment, each pin of the plurality of pins 500 is attached to the driving member 400 such that each pin only travels through one side of the main body 100, first endplate 200, second endplate 300, and the driving member 400.

Figure 10:
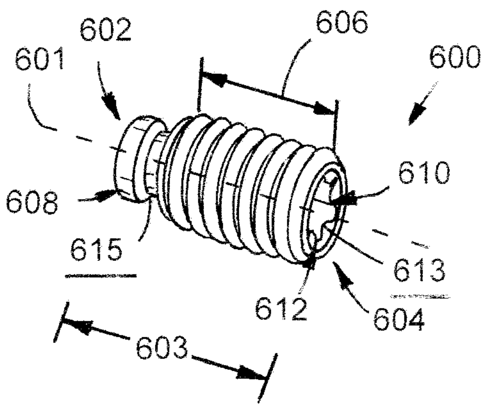
FIG. 10 is a perspective view of the actuation member of the first example expandable spacer illustrated in FIG. 1.

As shown in FIG. 10, the actuation member 600 has an actuation member first end 602, a length 603, an actuation member second end 604, a lengthwise axis 601 that extends from the actuation member first end 602 to the actuation member second end 604, a thread 606, a cam 608, and an actuation member recess 610. The length 603 of the actuation member 600 is measured from the actuation member first end 602 to the actuation member second end 604. The cam 608 is sized and configured to be disposed within the driving member channel 430. When assembled, the cam 608 is inserted into the driving member channel 430 before the plurality of pins 500 is inserted into the expandable spacer 100 for ease of assembly. The inclusion of cam 608 provides a mechanism for allowing the actuation member 600 to transition the driving member 400 towards the first lateral wall 106 of the main body 100, which, in turn, moves the expandable spacer 10 between the first configuration to the second configuration.

The actuation member recess 610 has a series of facets 612 and an actuation member inner surface 613. The actuation member recess 610 extends from the actuation member second end 604 towards the actuation member first end 602. The actuation member recess 610 is sized and configured to receive a driving tool (not illustrated) to assist in rotating and transitioning the actuation member 600 from a first position to a second position such that the expandable spacer 600 transitions from a first configuration to a second configuration. The actuation member recess 610 can have any suitable size, shape, and/or configuration, and selection of a suitable size, shape, and/or configuration for a driving member recess can be based on various considerations, including the size of the driving tool. Examples driving member recess configurations considered suitable include, but are not limited to, hexagonal, triangular, square, pentagonal, slotted, cross-recesses, Philips, hex socket, Philips-square, or any other driving member recess considered suitable for a particular application. In the illustrated embodiment, the driving member recess 610 illustrates a star-shaped configuration.

The thread 606 extends along a portion of the actuation member 600 between the actuation member first end 602 and the actuation member second end 604 and is circumferentially disposed around the portion of the actuation member outer surface 615. The thread 606 is sized and configured to be inserted into the groove 156 of the threaded opening 114 to move the actuation member 600 from a first position to a second position.

In use, the expandable spacer 10 has first and second configurations. Each of the FIGS. 1, 3, 6, and 7 illustrates the expandable spacer 10 in the first, contracted configuration. In the first configuration, the first endplate 200 is in contact with and adjacent to the main body 100 such that the first endplate bottom surface 211 contacts with the main body top surface 119. Additionally, the first and second extensions 206, 208 are disposed in the main body interior chamber 116, the first extension outer surface 237 contacts the third extension 306, and the first extension outer surface 257 contacts the fourth extension 308. In the second configuration, the first endplate bottom surface 211 does not contact the main body top surface 119, the first and second extensions 206, 208 are disposed in the main body interior chamber 116, the first extension outer surface 237 contacts the third extension 306, and the first extension outer surface 257 contacts the fourth extension 308.

When the expandable spacer 10 is in its first configuration, the expandable spacer 10 has a first height 11. When the expandable spacer 10 is in its second configuration, the expandable spacer 10 has a second height 13 that is greater than the first height.

When the expandable spacer 10 is in its first configuration, the second endplate 300 is in contact with and adjacent to the main body 100 such that the second endplate bottom surface 311 contacts with the main body bottom surface 121. Additionally, the first and second extensions 306, 308 are disposed in the main body interior chamber 116 and the first extension outer surface 337 and first extension outer surface 357 contact with the main body inner surface 115. In the second configuration, the second endplate bottom surface 311 does not contact the main body bottom surface 121, the first and second extensions 306, 308 are disposed in the main body interior chamber 116, and the first extension outer surface 337 and first extension outer surface 357 contact with the main body inner surface 115.

When the expandable spacer 10 is in its first configuration, the first extension 206 of the first endplate 200 is disposed within the slots 350, 352 of the second endplate 300 and the second extension 208 of the first endplate 200 is dispose within the slots 354, 356 of the second endplate 300. When the expandable spacer 10 is in its second configuration, the first extension 206 of the first endplate 200 is not disposed within the slots 350, 352 of the second endplate 300 and the second extension 208 of the first endplate 200 is not dispose within the slots 354, 356 of the second endplate 300. When the expandable spacer 10 is in its first configuration, the third extension 306 of the second endplate 300 is disposed within the slots 250, 252 of the first endplate 200 and the fourth extension 308 of the second endplate 300 is dispose within the slots 254, 256 of the first endplate 200. When the expandable spacer 10 is in its first configuration, the third extension 306 of the second endplate 300 is not disposed within the slots 250, 252 of the first endplate 200 and the fourth extension 308 of the second endplate 300 is not dispose within the slots 254, 256 of the first endplate 200. This structural configuration provides a mechanism that allows a user, such as a surgeon, to insert an expandable spacer into a narrow intravertebral disc space to maximize the intervertebral disc spacing and restore spinal stability.

Furthermore, when the expandable spacer 10 is in its first configuration, the driving member 400 is disposed inside of the main body interior chamber 116 and is connected to the actuation member 600 such that the actuation member 600 can move relative to the main body 100. In the illustrated embodiment, the cam 608 is disposed within the driving member channel 430. In addition, a portion of the thread 606 of the actuation member 600 is disposed inside of the threaded opening 114.

As illustrated in FIGS. 1, 2, 3, 4, 5, 6, 7, 23, and 24 the plurality of pins 500 contacts and links the main body 100, the first endplate 200, the second endplate 300, and the driving member 400 together. As described above, each pin of the plurality of pins 500 may be inserted into either the first set of openings on the third lateral wall of the main body 100 or the second set of openings on the fourth lateral wall of the main body 100 to link and assemble the expandable spacer 10. For example, in the illustrated embodiment, a pin 500 is disposed through each of openings 170, 180, 230, 251, 330, 351. An expandable spacer can be configured in any suitable manner according to a particular embodiment based on various considerations, including the anatomy of the spinal column in which it will be implanted and the desirability of the use of a driving member. In example embodiments, the expandable spacer may have one, two, three, or more than three configurations. In example embodiments, the planes may be at obtuse or acute angles relative to one another, or may be parallel to one another.

Figure 22:
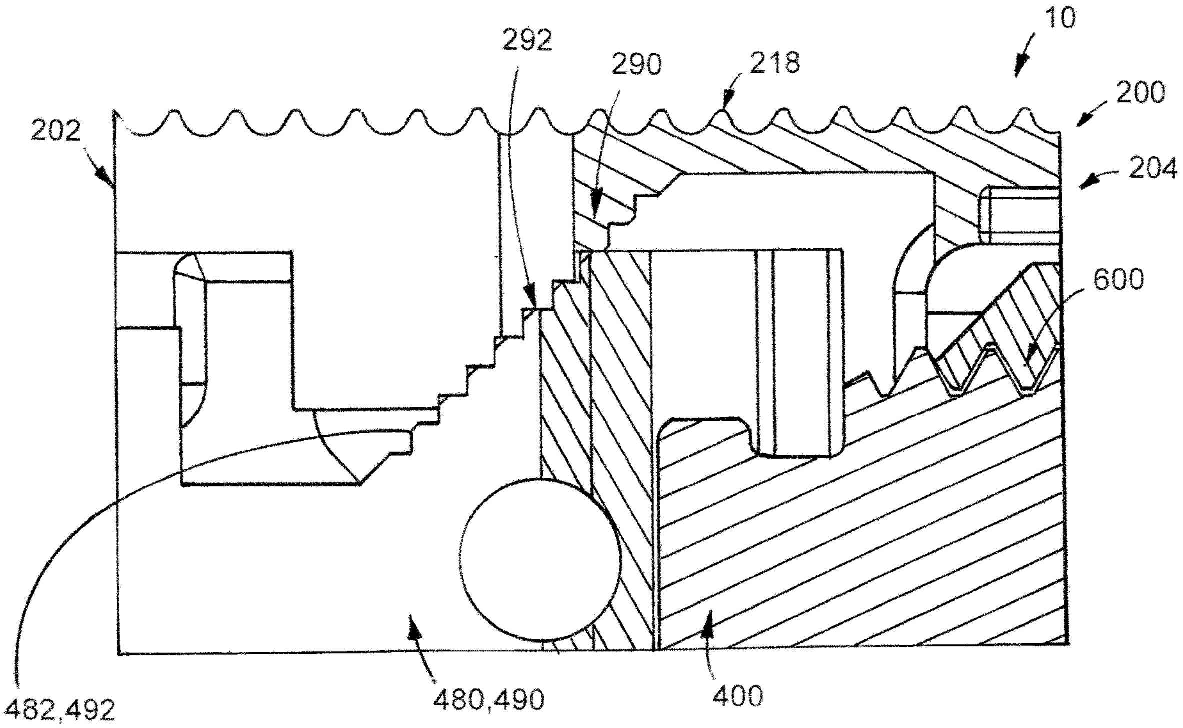
FIG. 22 is another partial sectional view of the first example expandable spacer illustrated in FIG. 1. The expandable spacer is shown in the second configuration.
Figure 23:
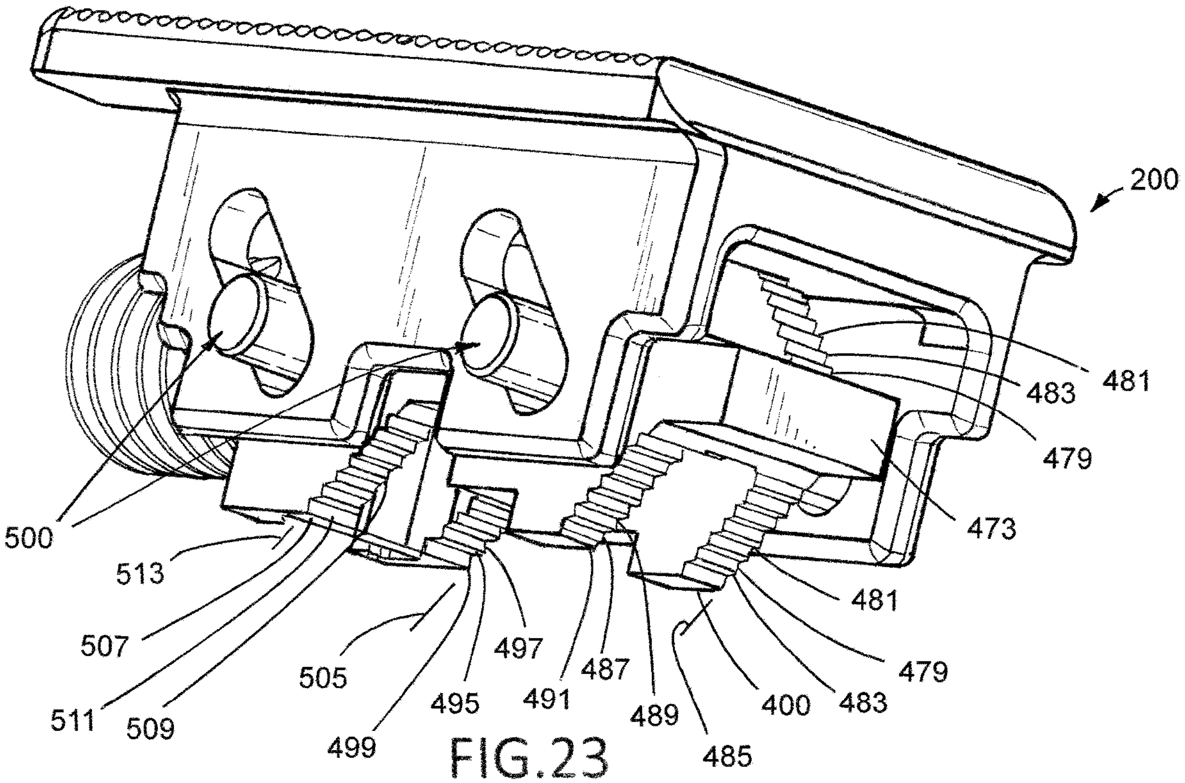
FIG. 23 is a perspective view of the first endplate, the driving member, and the plurality of pins of the first example expandable spacer illustrated in FIG. 1. The first endplate, the driving member, and the plurality of pins are each shown between the first and second positions.
Figure 24:
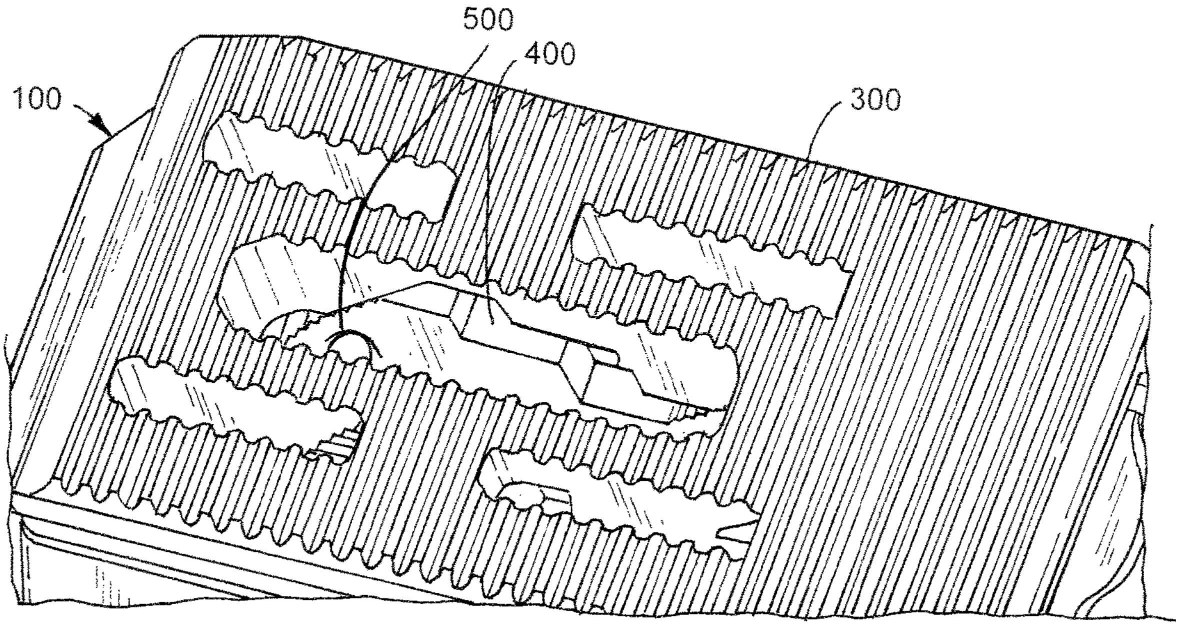
FIG. 24 is a partial perspective view of the first example expandable spacer illustrated in FIG. 1. The expandable spacer is shown between the first configuration and the second configuration.

FIGS. 4, 5, and 22 illustrate the expandable spacer 10 in its second configuration. To move the expandable spacer 10 to this configuration from the first configuration, a user, such as a surgeon, exerts a rotational force onto the actuation member 600 such that the actuation member 600 rotates clockwise to allow the actuation member 600 to move from a first position to a second position. In the first position, the first end 602 of the actuation member 600 is disposed a first distance from the main body first end 102. In the second position, the first end 602 of the actuation member 600 is disposed a second distance from the main body first end 102 that is less than the first distance. The transition of the actuation member 600 from its first position to its second position moves the driving member 400 to its second position, which, in turn, moves the expandable spacer 10 to its second configuration. The crossing patterns of the first and second sets of openings 230, 251 of the first endplate 200 and the third and fourth sets of openings 330, 351 of the second endplate 300 allow the plurality of pins 500 to extend the first and second endplates 200, 300 away from the main body 100 in opposite directions when a force is applied by the driving member 400 and the actuation member 600. Since the first, second, third, and fourth angles of the first, second, third and fourth set of openings 230, 251, 330, 351 of the first and second endplates 200, 300 are the same angles, the first and second endplates 200, 300 remain parallel to each other when the expandable spacer 10 is moved from the first configuration to the second configuration.

When the driving member 400, the plurality of pins 500, and the actuation member 600 reach the second position, the expandable spacer 10 is in its second configuration and has a second height 13. In this embodiment, the second height 13 of the expandable spacer 10 is greater than the first height 11 when the expandable spacer 10 is in the first configuration. In this embodiment, the first height is about 8 millimeters and the second height is about at 13 millimeters. While specific heights have been illustrated, an expandable spacer can have any suitable height in its first configuration or its second configuration and selection of a suitable height can be based on various considerations, including the height of the disk space, the height need to maintain stability in the spinal column, and other consideration. Examples of suitable first heights for an expandable spacer include heights between about 7 millimeters and about 8 millimeters, and examples of suitable second heights for an expandable spacer include heights between about 11 millimeters and about 13 millimeters.

In the second configuration, a user, such as a surgeon, optionally can place a material into the expandable spacer 10 to fill in all gaps and spaces inside the expandable spacer 10, such as the driving member interior chamber 416, the main body interior chamber 116, and other suitable positions, to maintain the expandable spacer in the second configuration and allow for stability in the spinal column. The material used may include any material suitable for inclusion in an expandable spacer and selection of a suitable material can be based on various considerations, including the overall width of the disk space. Examples of suitable materials to introduce into an expandable spacer include allograft materials, autograft materials, or other suitable materials.

The expandable spacers, and components of the expandable spacers, described herein can be formed of any suitable material, including presently known and later-developed materials for use in implantable medical devices and considered suitable for implantation in spaces between bones, including within intervertebral spaces. Selection of an appropriate material for each component of an expandable spacer (e.g., main body 100, the first endplate 200, the second endplate 300, the driving member 400, the plurality of pins 500, the actuation member 600) can be based on various considerations, including the degree to which is desired to visualize the device using visualization techniques and/or equipment subsequent to implantation, the type and/or quantity of bone graft, or other material, that may be used in conjunction with the expandable spacer during treatment, and/or the anatomical features at the location at which the expandable spacer is to be implanted. Examples of materials considered suitable to form an expandable spacer include biocompatible materials, materials that can be made biocompatible, polymers, polyetheretherketone ("PEEK"), metals, stainless steel, titanium, such as TI-6AL-4V ELI (Grade 23) per ASTM F3001, nickel-cobalt-chromium alloys, radiolucent materials, radiopaque materials, bone materials, combinations of the materials described herein, and any other material considered suitable for a particular embodiment.

The expandable spacers described herein can be formed using any suitable method or technique of manufacture. Selection of a suitable method or technique can be based on various considerations, such as the type of material that forms an expandable spacer. Examples of methods and techniques considered suitable to form an expandable spacer include conventional forming and/or manufacturing techniques, 3D-printing, fused deposition modeling, stereolithography, digital light processing, selective laser sintering, selective laser melting, electron beam melting, laminated object manufacturing, binder jetting, material jetting, wax casting, additive manufacturing techniques, combinations of the methods and/or techniques described herein, and any other method or technique considered suitable for a particular embodiment.

Figure 25:
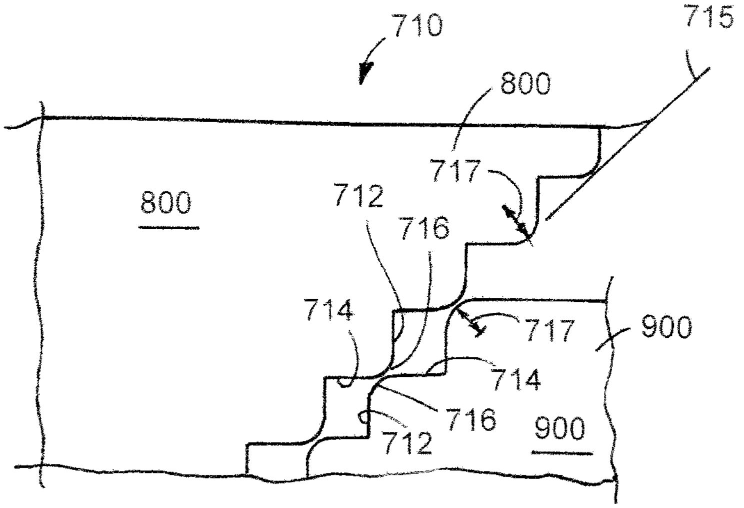
FIG. 25 is a partial side view of a portion of a second example expandable intervertebral spacer. The expandable spacer is shown between the first configuration and the second configuration.

FIG. 25 illustrates a portion of a second expandable spacer 710. The expandable spacer 710 is similar to the expandable spacer 10 illustrated in FIGS. 1 through 24 and described above, except as detailed below. The expandable spacer 710 is moveable between a first configuration and a second configuration.

In the illustrated embodiment, each step defined by the components of the expandable spacer 710 includes a step first surface 712, a step second surface 714, and a step curved surface 716. The step first surface 712 and the step second surface 714 cooperatively define a slope 715 that extends between each step curved surface 716. The step curved surface 716 has a radius of curvature 717. A step curved surface can have any suitable radius of curvature and selection of a suitable radius of curvature can be based on various considerations, such as the intended use of the expandable spacer. As shown in FIG. 25, the structural configuration of the steps has been incorporated into the first endplate 800 and the driving member 900 such that when the expandable spacer 710 is between the first and second configurations, the step curved surfaces 716 contact one another. This structural arrangement provides a mechanism to move the expandable spacer 710 between its first and second configurations in a manner that is different than embodiments that include faceted surfaces on each step.

While the structural configuration of the step first surface 712, the step second surface 714, and the step curved surface 716 have been illustrated as being incorporated on a first endplate 800 and a driving member 900, the structural arrangement of steps described in FIG. 25 can be included on any suitable portion of an expandable spacer. Selection of a suitable portion of an expandable spacer to include step curved surfaces can be based on various considerations, including the intended use of the expandable spacer. Examples of suitable portions of an expandable spacer to include step curved surfaces include a portion, or the entirety, of a first endplate, a second endplate, a driving member, a first extension (e.g., first extension 206, first extension 460), a second extension (e.g., second extension 208, second extension 470), a third extension (e.g., third extension 306, third extension 480), a fourth extension (e.g., fourth extension 308, fourth extension 490), and any other portion of an expandable spacer considered suitable for a particular embodiment.

Figure 26:
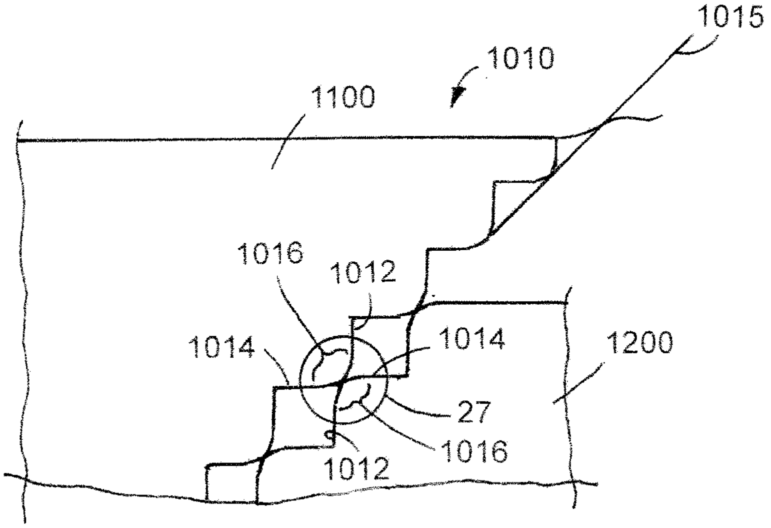
FIG. 26 is a partial side view of a portion of a third example expandable intervertebral spacer. The expandable spacer is shown between the first configuration and the second configuration.
Figure 27:
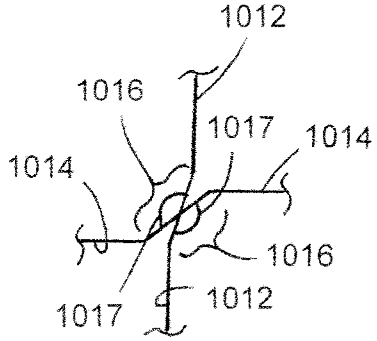
FIG. 27 is a magnified view of Area 27 shown in FIG. 26.

FIGS. 26 and 27 illustrate a portion of a third expandable spacer 1010. The expandable spacer 1010 is similar to the expandable spacer 10 illustrated in FIGS. 1 through 24 and described above, except as detailed below. The expandable spacer 1010 is moveable between a first configuration and a second configuration.

In the illustrated embodiment, each step defined by the components of the expandable spacer 1010 includes a step first surface 1012, a step second surface 1014, and a step multi-faceted portion 1016. The step first surface 1012 and the step second surface 1014 cooperatively define a slope 1015 that extends between each step multi-faceted portion 1016. The step multi-faceted portion 1016 has a two surfaces disposed at an angle 1017 relative to one another. A step multi-faceted portion can have any suitable number of surfaces disposed at any suitable angle relative to one another and selection of a suitable number of surfaces and a suitable angle to disposed adjacent surfaces relative to one another can be based on various considerations, such as the intended use of the expandable spacer. Examples of suitable numbers of surfaces to include in a multi-faceted portion include two, a plurality, three, four, five, more than five, more than ten, and any other number considered suitable for a particular embodiment.

As shown in FIGS. 26 and 27, the structural configuration of the steps has been incorporated into the first endplate 1100 and the driving member 1200 such that when the expandable spacer 1010 is between the first and second configurations, the step multi-faceted portions 1016 contact one another. This structural arrangement provides a mechanism to move the expandable spacer 1010 between its first and second configurations in a manner that is different than embodiments that include a single faceted surface on each step or a curved surface on each step. While the structural configuration of the step first surface 1012, the step second surface 1014, and the step multi-faceted portion 1016 have been illustrated as being incorporated on a first endplate 1100 and a driving member 1200, the structural arrangement of steps described in FIGS. 26 and 27 can be included on any suitable portion of an expandable spacer. Selection of a suitable portion of an expandable spacer to include step multi-faceted portion can be based on various considerations, including the intended use of the expandable spacer. Examples of suitable portions of an expandable spacer to include step multi-faceted portions include a portion, or the entirety, of a first endplate, a second endplate, a driving member, a first extension (e.g., first extension 206, first extension 460), a second extension (e.g., second extension 208, second extension 470), a third extension (e.g., third extension 306, third extension 480), a fourth extension (e.g., fourth extension 308, fourth extension 490), and any other portion of an expandable spacer considered suitable for a particular embodiment.

Any of the faceted surfaces, curved surfaces, and/or multi-faceted portions (e.g., step intermediate portion) described herein can be combined in any suitable manner and included on a portion, or the entirety, of a first endplate, a second endplate, a driving member, a first extension (e.g., first extension 206, first extension 460), a second extension (e.g., second extension 208, second extension 470), a third extension (e.g., third extension 306, third extension 480), and/or a fourth extension (e.g., fourth extension 308, fourth extension 490). For example, a first portion of a first extension (e.g., first extension 206, first extension 460), a second extension (e.g., second extension 208, second extension 470), a third extension (e.g., third extension 306, third extension 480), and/or a fourth extension (e.g., fourth extension 308, fourth extension 490) can include a first type of step portion (e.g., faceted surface, curved surface, and/or multi-faceted portion) and a second portion of the first extension (e.g., first extension 206, first extension 460), the second extension (e.g., second extension 208, second extension 470), the third extension (e.g., third extension 306, third extension 480), and/or the fourth extension (e.g., fourth extension 308, fourth extension 490) can include a second type of step portion (e.g., faceted surface, curved surface, and/or multi-faceted portion) that is different than the first type of step portion. A faceted surface included on a plurality of steps can be disposed at any suitable angle relative to a first step surface and a second step surface and selection of a suitable angle to position a faceted surface relative to a first step surface and/or a second step surface can be based on various considerations, including the intended use of the expandable spacer. Examples of angles considered suitable between a faceted surface and a first step surface and/or a second step surface include angles equal to, less than, greater than, or about 15 degrees, 30 degrees, 45 degrees, 60 degrees, 75 degrees, between about 15 degrees and about 75 degrees, between about 30 degrees and about 60 degrees, and any other angle considered suitable for a particular embodiment.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventor simply to describe and illustrate examples of the invention and are not intended to limit the scope of the invention or its protection, which is to be given the full breadth of the appended claims and any and all equivalents thereof.

What is claimed is:

1. An expandable intervertebral spacer having a first configuration and a second configuration, the expandable intervertebral spacer comprising:

a main body defining a main body interior chamber;

a first endplate partially disposed within the main body interior chamber and having a first endplate top, a first endplate bottom, and a first endplate first protruding member extending from the first endplate bottom and away from the first endplate top;

a second endplate partially disposed within the main body interior chamber and having a second endplate top, a second endplate bottom, and a second endplate first protruding member extending from the second endplate bottom and away from the second endplate top;

a driving member having a driving member first extension interfacing with the first endplate first protruding member and the second endplate first protruding member;

an actuation member partially disposed within the driving member and moveable between a first position and a second position, said expandable intervertebral spacer in said first configuration when the actuation member is in the first position, said expandable intervertebral spacer in said second configuration when the actuation member is in the second position; and a plurality of pins, each pin of the plurality of pins extending through the main body, the first endplate, the second endplate, and the driving member.

2. The expandable intervertebral spacer of claim 1, wherein the first endplate first protruding member defines a first plurality of steps.

3. The expandable intervertebral spacer of claim 2, wherein each step of the first plurality of steps has a curved surface.

4. The expandable intervertebral spacer of claim 2, wherein each step of the first plurality of steps has a multi-faceted portion.

5. The expandable intervertebral spacer of claim 2, wherein the second endplate first protruding member defines a second plurality of steps.

6. The expandable intervertebral spacer of claim 1, wherein said expandable spacer has a first height between the first and second endplates in the first configuration and second height between the first and second endplates in the second configuration, the second height being greater than the first height.

7. The expandable intervertebral spacer of claim 1, wherein the first endplate has a first endplate first extension extending from the first endplate bottom and away from the first endplate top.

8. The expandable intervertebral spacer of claim 7, wherein the second endplate defines a second endplate slot; and wherein the first endplate first extension is partially disposed within the second endplate slot when the expandable spacer is in the first configuration.

9. The expandable intervertebral spacer of claim 7, wherein the first endplate has a lengthwise axis; and wherein the first endplate first extension includes a first set of openings, each opening of the first set of openings positioned at a first angle relative to a plane that is parallel to the lengthwise axis of the first endplate.

10. The expandable intervertebral spacer of claim 1, wherein the second endplate has a second endplate first extension extending from the second endplate bottom and away from the second endplate top.

11. The expandable intervertebral spacer of claim 10, wherein the first endplate defines a first endplate slot; and wherein the second endplate first extension is partially disposed within the first endplate slot when the expandable spacer is in the first configuration.

12. The expandable intervertebral spacer of claim 10, wherein the second endplate has a lengthwise axis; and wherein the second endplate first extension includes a second set of openings, each opening of the second set of openings positioned at a second angle relative to a plane that is parallel to the lengthwise axis of the first endplate.

13. The expandable intervertebral spacer of claim 1, wherein the first endplate has a first endplate first extension and a first endplate second extension, each of the first endplate first extension and the first endplate second extension extending from the first endplate bottom and away from the first endplate top; and wherein the first endplate first protruding member is disposed between the first endplate first extension and the first endplate second extension.

14. The expandable intervertebral spacer of claim 1, wherein the second endplate has a second endplate first extension and a second endplate second extension, each of the second endplate first extension and the second endplate second extension extending from the second endplate bottom and away from the second endplate top; and wherein the second endplate first protruding member is disposed between the second endplate first extension and the second endplate second extension.

15. The expandable intervertebral spacer of claim 1, wherein the first endplate has a first endplate second protruding member;

wherein the second endplate has a second endplate second protruding member; and wherein the driving member has a driving member second extension, a driving member third extension, and a driving member fourth extension.

16. The expandable intervertebral spacer of claim 15, wherein the driving member first extension interfaces with the first endplate first protruding member and the second endplate first protruding member;

wherein the driving member second extension interfaces with the first endplate first protruding member and the second endplate first protruding member;

wherein the driving member third extension interfaces with the first endplate second protruding member and the second endplate second protruding member; and wherein the driving member fourth extension interfaces with the first endplate second protruding member and the second endplate second protruding member.

* * * * *